(12) United States Patent
Schneider et al.

(10) Patent No.: US 11,266,783 B2
(45) Date of Patent: Mar. 8, 2022

(54) INJECTION DEVICE, SYSTEM, AND METHOD FOR USE

(71) Applicant: DJ Medical, LLC, Burnsville, MN (US)

(72) Inventors: Daniel Schneider, Minneapolis, MN (US); Troy A. Pongratz, Minneapolis, MN (US)

(73) Assignee: DJ Medical, LLC, Burnsville, MN (US)

( * ) Notice: Subject to any disclaimer, the term of this patent is extended or adjusted under 35 U.S.C. 154(b) by 0 days.

(21) Appl. No.: 17/148,555

(22) Filed: Jan. 13, 2021

(65) Prior Publication Data
US 2021/0228808 A1 Jul. 29, 2021

Related U.S. Application Data

(60) Provisional application No. 62/960,538, filed on Jan. 13, 2020.

(51) Int. Cl.
*A61M 5/315* (2006.01)
*A61M 5/28* (2006.01)
(Continued)

(52) U.S. Cl.
CPC ......... *A61M 5/281* (2013.01); *A61K 38/4893* (2013.01); *A61M 5/002* (2013.01);
(Continued)

(58) Field of Classification Search
CPC .......... A61M 5/28; A61M 5/281; A61M 5/20; A61M 2005/206; A61M 5/2033; A61M 2005/2073; A61M 2005/208; A61M 5/315
See application file for complete search history.

(56) References Cited

U.S. PATENT DOCUMENTS 5,137,516 A * 8/1992 Rand .................. A61M 5/2033
604/136
2008/0119958 A1 5/2008 Bear et al.
(Continued)

FOREIGN PATENT DOCUMENTS

GB 2447046 A 7/2011
WO WO 03/068290 A2 8/2003
(Continued)

OTHER PUBLICATIONS

Communication Pursuant to Article 94(3) EPC for related EP application No. 17812122.4 dated Sep. 10, 2020, 8 pages.
(Continued)

*Primary Examiner* — Deanna K Hall
(74) *Attorney, Agent, or Firm* — Winthrop & Weinstine, P.A.; Nadeem W. Schwen; Alicia Griffin Mills

(57) ABSTRACT

An injection device for the self-administration of an injection of solution that includes a body portion/handle configured for engagement with a cartridge containing the solution and an injection needle. The injection device includes a safety mechanism whereby ejection of solution from the injection device cannot be done unless the safety mechanism is released. The injection device further involves two-stage deployment whereby a needle may be inserted upon release of the safety mechanism and solution is injected upon full insertion of the needle.

16 Claims, 23 Drawing Sheets

(51) Int. Cl.
*A61M 5/32* (2006.01)
*A61K 38/48* (2006.01)
*A61M 5/42* (2006.01)
*A61M 5/00* (2006.01)
*A61M 5/20* (2006.01)

(52) U.S. Cl.
CPC .......... *A61M 5/008* (2013.01); *A61M 5/2033* (2013.01); *A61M 5/3158* (2013.01); *A61M 5/31571* (2013.01); *A61M 5/3202* (2013.01); *A61M 5/422* (2013.01)

(56) References Cited

U.S. PATENT DOCUMENTS

| | | |
|---|---|---|
| 2012/0221036 A1 | 8/2012 | Ahmann et al. |
| 2014/0324021 A1 | 10/2014 | Ulrich et al. |
| 2015/0201880 A1 | 7/2015 | Bureau et al. |
| 2016/0228642 A1 | 8/2016 | Cowe |
| 2016/0287788 A1 | 10/2016 | Tremblay et al. |
| 2016/0331900 A1 | 11/2016 | Wei |
| 2017/0281877 A1 | 10/2017 | Marlin et al. |
| 2017/0340840 A1 | 11/2017 | Sweis |
| 2018/0133403 A1 | 5/2018 | Schneider et al. |
| 2018/0147352 A1* | 5/2018 | Farmer .............. A61M 5/2033 |

FOREIGN PATENT DOCUMENTS

| | | |
|---|---|---|
| WO | WO 2010/018411 A1 | 2/2010 |
| WO | WO 2017/220553 A1 | 12/2017 |

OTHER PUBLICATIONS

International Search Report for related International Application No. PCT/US2017/062000 dated Feb. 14, 2018, 7 pages.
Written Opinion for related International Application No. PCT/US2017/062000 dated Feb. 14, 2018, 9 pages.
International Search Report for corresponding International Application No. PCT/US2021/013332, dated Mar. 25, 2021, 2 pages.
Written Opinion for corresponding International Application No. PCT/US2021/013332, dated Mar. 25, 2021, 5 pages.
Final Office Action for corresponding U.S. Appl. No. 15/815,026; dated Aug. 26, 2021; 19 pages.

* cited by examiner

INJECTION DEVICE, SYSTEM, AND METHOD FOR USE

CROSS-REFERENCE TO RELATED APPLICATIONS

The present application claims the benefit of U.S. Provisional Application No. 62/960,538, filed on Jan. 13, 2020. The present application is also related to U.S. patent application Ser. No. 15/815,026 entitled Self-Administered Injection Device and Method, filed on Nov. 16, 2017; U.S. Provisional Application 62/422,686 entitled Systems and Methods for Self-Administration of Botulinum Toxin, filed on Nov. 16, 2016; and U.S. Provisional Application No. 62/532,052 entitled Systems and Methods for Self-Administration of Botulinum Toxin, filed on Jul. 13, 2017, the contents of which are incorporated by reference herein in their entireties.

FIELD OF THE INVENTION

The present application relates to a method and system for self-administration of an injectable substance such as botulinum toxin, vaccinations, in vitro fertilization medicines, chronic illness treatment medicines, flu shots, insulin, or other medicinal or cosmetic treatment substances. More particularly, the present application relates to a method and system for self-administration of an injectable substance at or around the facial area. Still more particularly, the present application relates to a method and system for self-administration of an injectable substance at or near the eye and forehead area.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In many contexts, injections of medicine are performed by trained professionals. For example, vaccinations, flu shots, antibiotics, and other medicines are commonly administered by nurses, physician assistants, doctors, or other trained professionals. In some cases, where injection of medicine is performed on a regular or relatively frequent periodic basis, patients may learn to administer injections on their own. For example, individuals with diabetes may learn to regularly administer insulin to control blood sugar levels in their system. These individuals may also regularly test their blood sugar levels to determine whether there is a need for an injection. Other examples include patients with chronic illnesses such as multiple sclerosis, for example. In these contexts, the patient may become relatively well versed in and comfortable with the injection process due to the repetition of the procedure. In general, the precise location of the injection is not important for these purposes.

Botulinum toxin is a substance used for various purposes, including both medical and cosmetic purposes. Medical uses may include treating medical conditions such as hyperhidrosis and migraine headaches. In some cosmetic applications, botulinum toxin is used to relax muscles, such as facial muscles, in order to reduce the appearance and/or the formation of lines or wrinkles in the skin or otherwise smooth the appearance of skin, for example around an individual's eyes, forehead, mouth, neck, scalp, or other areas of the face or body.

Botulinum toxin, which may be provided under the brand name BOTOX, DYSPORT, XEOMIN, or other names, is typically applied by injection. A syringe is filled with a desired amount of the botulinum toxin and injected into a muscle or other tissue. Generally, botulinum toxin injected for medical or cosmetic purposes is injected by a medical professional, such as a physician or a nurse or aesthetician practicing under the guidance of a physician. This is, in part, because the location of the administration is important with respect to the aesthetic effect of the injection. Still further, the amount of the injected substance also affects the resulting cosmetic result. Moreover, these types of injections are not commonly performed on a frequent basis and, as such, the patient does not have the opportunity to become comfortable with the process.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present application relates to a method and system for self-administration of an injectable substance or solution such as botulinum toxin, vaccinations, in vitro fertilization medicines, chronic illness treatment medicines, flu shots, insulin, or other medicinal or cosmetic treatment substances. More particularly, the present application relates to a method and system for self-administration of an injectable substance at or around the facial area. Still more particularly, the present application relates to a method and system for self-administration of an injectable substance at or near the eye and forehead area.

In one embodiment, the present disclosure relates to an injection device for the self-administration of an injection of solution that includes a body portion/handle configured for engagement with a cartridge containing the solution and an injection needle. The injection device includes a safety mechanism whereby ejection of solution from the injection device cannot be done unless the safety mechanism is released. The injection device further involves two-stage deployment whereby a needle may be inserted upon release of the safety mechanism and solution is injected upon full insertion of the needle.

In one embodiment an injection device for injection of a solution is provided. The injection device includes a body portion and a cartridge removably couplable to the body portion. The body portion includes a cartridge end and a handle end and comprises a main body, an injection assembly, and actuation button, and a safety assembly. The injection assembly extends through the main body to the cartridge end and effects insertion of a needle and ejection of the solution. Actuation of the actuation button leads to insertion of the needle and dispensing of the solution. The safety mechanism being configured to prevent insertion of the needle and/or dispensing of the solution. The cartridge comprises a syringe assembly, the needle, and a needle shield over the needle. The syringe assembly includes a drug chamber and a piston, wherein the drug chamber houses the solution. The safety mechanism is released upon depression of the needle shield such that the needle may be inserted and the solution dispensed.

In some embodiments, the injection device has multi stage deployment comprising insertion of the needle and injection of the solution and the multi stage deployment may be activated by actuating the actuation button. The injection assembly may work with the piston of the cartridge to dispense the solution. The body portion may further comprise a cocking assembly comprising a cocking handle, an end cap, a cocking ring, and a snap ring. The cocking assembly is provided at the handle end of the body portion. The cartridge may further comprise a safety assembly including a safety interlock wherein when the safety interlock is in a used configuration, the needle shield is locked in a forward position and the cartridge cannot be reused. The injection assembly may further comprise a needle insertion spring and a drug delivery spring. The cartridge may include an extension piece and the body portion may include an opening piece, wherein the extension piece is received by the opening piece to removably couple the cartridge to the body portion. The cartridge may be predosed with a specific quantity of solution.

In another embodiment, an injection device for injection of a solution is provided. The injection device includes a body portion and a cartridge removably couplable to the body portion. The body portion may comprise an injection assembly and a safety mechanism. The injection assembly effects insertion of a needle and ejection of the solution. The safety mechanism being configured to prevent insertion of a needle and/or dispensing of a solution. The cartridge may comprise a syringe assembly, a safety mechanism, a needle, and a needle shield positioned over the needle. The syringe assembly may include a drug chamber and a piston, wherein the drug chamber houses the solution. The safety mechanism may be released upon proper positioning of the injection device, wherein such release enables the needle to be inserted and the solution to be dispensed. Proper positioning may be indicated by depression of the needle shield.

In some embodiments, the body portion may further comprise an actuation button, wherein actuation of the actuation button leads to insertion of the needle and dispensing of the solution. In some embodiments, the actuation button cannot be actuated until the safety mechanism is released. The drug chamber may be formed of glass and other portions of the cartridge may be formed of plastic. The injection device may have multi stage deployment comprising insertion of the needle and injection of the solution. The multi stage deployment is triggered by actuation of the actuation button.

In yet another embodiment, an injection kit for injection of a solution is provided. The injection kit may comprise an injection device, a staging tray, and an injection template. The injection device may comprise a body portion and a cartridge, the cartridge being removably couplable to the body portion. The body portion may have a cartridge end and a handle end and may comprise an injection assembly, a safety mechanism, and an actuation button. The safety mechanism may be configured to prevent insertion of a needle and/or dispensing of a solution. Actuation of the actuation button may lead to insertion of the needle and dispensing of the solution. The cartridge includes a syringe assembly, a needle, and a needle shield. The syringe assembly includes a drug chamber and a piston, wherein the drug chamber houses the solution. The safety mechanism is released upon depression of the needle shield such that the needle may be inserted and the solution dispensed. The staging tray includes positions for receiving one or more cartridges. The injection template has holes for receiving the needle.

In some embodiments, the positions on the staging tray correspond with injection locations on a body and wherein the cartridges are preloaded on the tray. Further, the injection template may correspond with a location on a body and the holes align with injection sites at that location. The injection kit may include a numbing agent.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 3 illustrates a perspective view of a kit including an injection device, a staging tray, and a plurality of cartridges, according to one or more embodiments.

FIG. 4*a* illustrates an injection device, in accordance with one embodiment.

FIG. 4*b* illustrates an injection device, in accordance with one embodiment.

FIG. 5*a* illustrates the injection device with the cartridge disengaged from the body portion, in accordance with one embodiment.

FIG. 5*b* illustrates the injection device with the cartridge disengaged from the body portion, in accordance with one embodiment.

FIG. 6 illustrates an end view of the plate of the body portion, in accordance with one embodiment.

FIG. 7*a* illustrates a cross sectional view of the outer housing of the cartridge 204, in accordance with one embodiment.

FIG. 7*b* illustrates an end view of the outer housing of the cartridge, in accordance with one embodiment.

FIG. 8 illustrates an exploded view of the body portion of the injection device, in accordance with one embodiment.

FIG. 9 illustrates an exploded view of the cartridge of the injection device, in accordance with one embodiment.

FIG. 10*a* the outer housing of the cartridge, in accordance with one embodiment.

FIG. 10*b* the outer housing of the cartridge, in accordance with one embodiment.

FIG. 11*a* illustrates the exterior of the body portion/handle in the cocked position, in accordance with one embodiment.

FIG. 11*b* illustrates the interior of the body portion/handle of FIG. 11*a* along Section F-F.

DETAILED DESCRIPTION

Figure 1:
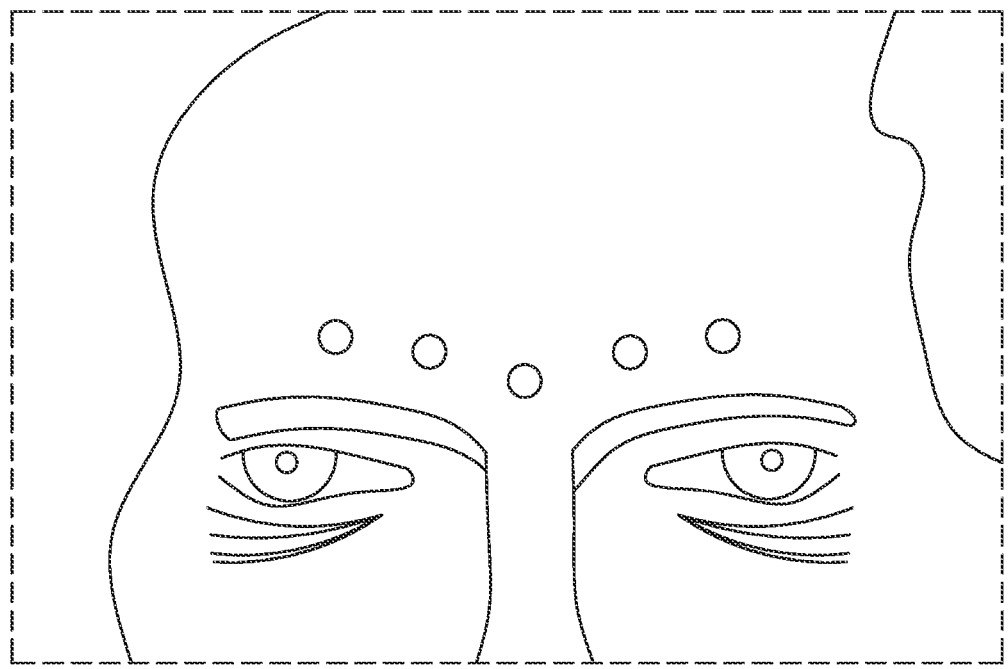
FIG. 1 illustrates a front view of a user's forehead, showing approximate locations for botulinum toxin injections, according to one or more embodiments.

The present application relates to a method and system for self-administration of an injectable substance such as insulin, botulinum toxin, chronic illness treatment medicines, flu shots, or other medicinal or cosmetic treatment substances. More particularly, the present application relates to a method and system for self-administration of an injectable substance at or around the facial area. Still more particularly, the present application relates to a method and system for self-administration of an injectable substance at or near the eye and forehead area.

The present disclosure relates to systems and methods for self-administration or administration to others of injections. It is to be appreciated that the systems, methods, devices, and kits disclosed herein facilitate injection of any substance by any user. In various embodiments these injections may be botulinum toxin injections, vaccinations, and medications. The systems and methods facilitate user injection of an injectable substance at specific and precise locations on the body. Particularly, the present disclosure, in one or more embodiments, relates to an injection device, a kit including the injection device and other accoutrements, and a method for using the injection device and/or kit. The injection device may be particularly adapted for use by a relatively untrained user and may provide for easy loading of pre-filled cartridges and safety mechanisms associated with exposing a needle and injecting a substance. In general, the injection device may use single use prefilled cartridges.

It is to be appreciated that while the systems and methods disclosed herein are specifically described with respect to self-administration of injections, the systems and methods may alternatively be used by a user to administer injections to another person. Thus, while the systems and methods are especially useful for self-administration, they are in no way limited to self-administration.

The kit may include a series of cartridges each containing a particular quantity of injectable substance (such as botulinum toxin), the injection device, a staging tray for arranging the cartridges before use, and one or more, such as a series of, injection patches. Components included in the kit may further the ability for a user to self-administer, or to administer to others, a solution without training or frequent use. In particular, the cartridges in the kit may have secluded or hidden needles for purposes of safety, but also for obstructing view of the needle for users uncomfortable with needles. The cartridges may be preloaded/dosed cartridges such that dosing is simple and straight forward. The cartridges and the injection device may work together for a simple reloading process and the staging tray may allow for arrangement of the cartridges in an area and/or order for ease of use. Finally, the injection patches/template may work with the injection device to help position the injection device prior to injection and the template may include a numbing agent to reduce pain or injection sensation. The injection patches or template may have openings or markings through which the needle is inserted.

Accordingly, the injection device and/or kit may be used to self-administer botulinum toxin injections efficiently with ease, low anxiety, low pain, high precision (dosage and location), and high accuracy (dosage and location). It is to be appreciated that while much of the present disclosure is focused on botulinum toxin injections, other injections may be performed with some or all of the devices described herein. For example, the injection device and/or kit may alternatively be used to self-administer vaccinations, medications (such as in vitro fertilization medications), and other.

Figure 2:
FIG. 2 illustrates a side view of a user's eye area, showing approximate locations for botulinum toxin injections, according to one or more embodiments.

Referring now to FIGS. 1 and 2, the present application, in one or more embodiments, relates to a device, kit, and/or method for self-administration of botulinum toxin injections. FIGS. 1 and 2 illustrate locations where a user may wish to self-inject botulinum toxin. FIG. 1 illustrates a front view of a user's forehead, showing approximate locations 10 for botulinum toxin injections, according to one or more embodiments. FIG. 2 illustrates a side view of a user's eye area, showing approximate locations 10 for botulinum toxin injections, according to one or more embodiments. A user may wish to inject botulinum toxin near the user's eye(s), forehead, neck, scalp, and/or any other suitable location. In other embodiments, other locations may be suitable for injection and/or other substances may be injected using the devices and/or kits described herein. The precise spacing of injection points may vary person-to-person based on the size of the injection area for that person.

Figure 3:
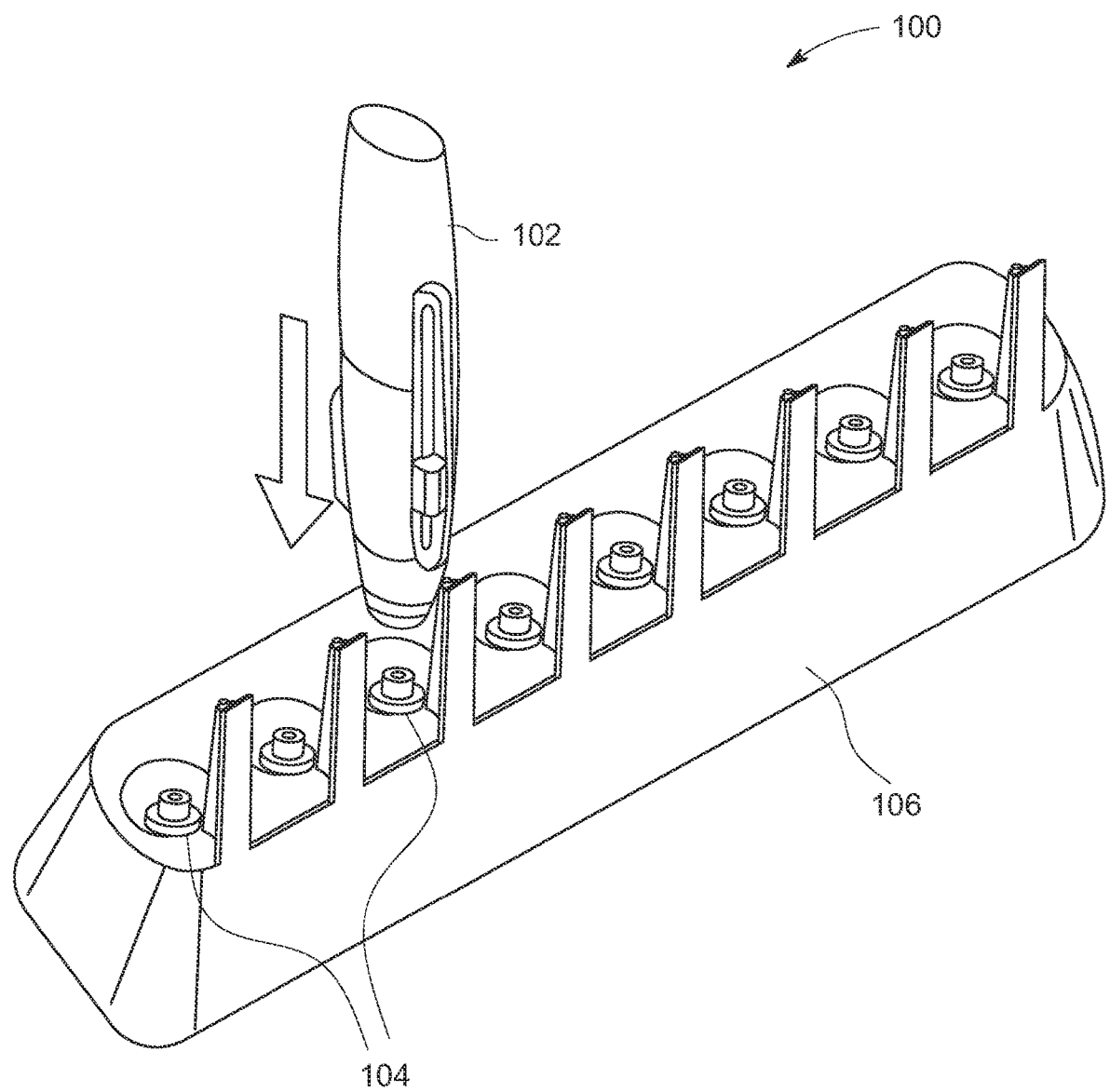

FIG. 3 illustrates a perspective view of a kit including an injection device, a staging tray, and a plurality of cartridges, according to one embodiment. As shown, the kit 100 may include an injection device 102, a series of cartridges 104, and a staging template or tray 106. The kit may further include a series of injection patches or templates, a numbing agent, and/or other useful components.

Injection Device

Embodiments an injection device 202 and cartridge 204 are shown in FIGS. 4a-10b.

Figure 4A:
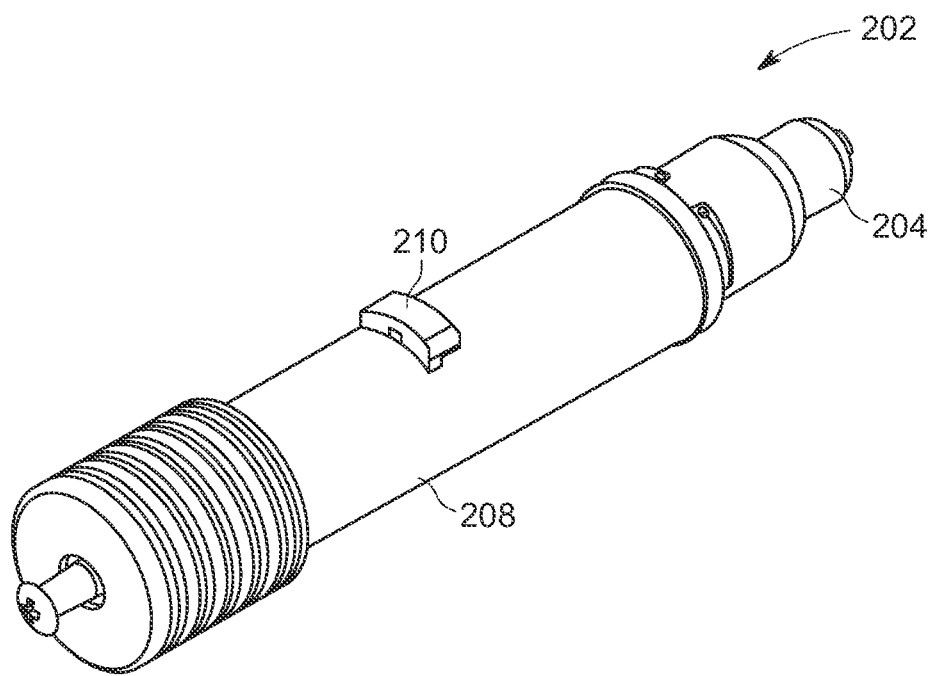
Figure 4B:
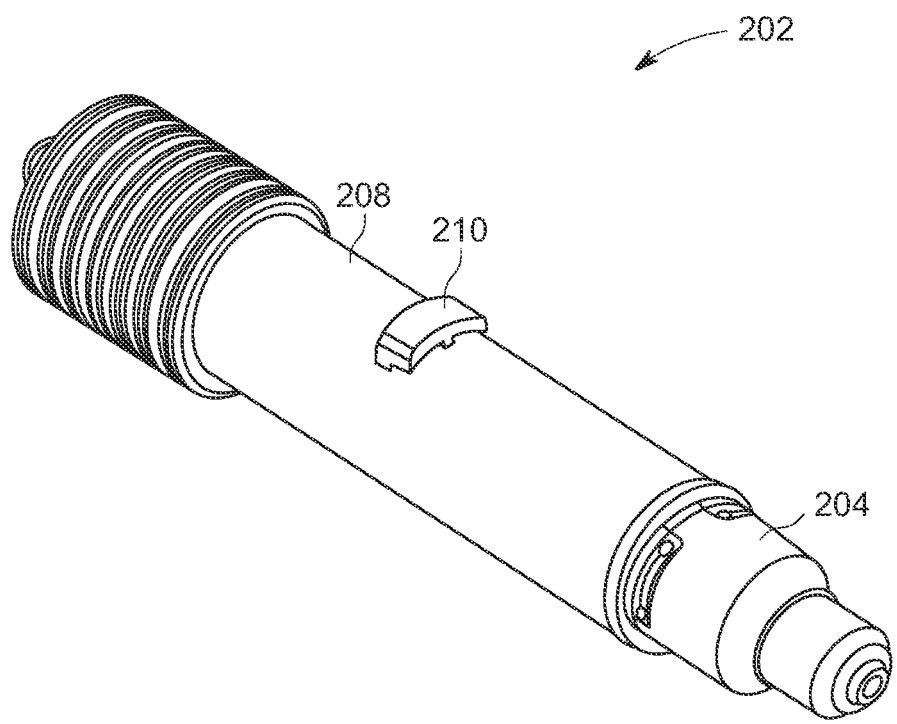

FIGS. 4a and 4b illustrate an injection device 202, in accordance with one embodiment. As shown, the injection device 202 may include a cartridge 204 and a body portion or handle 208. The cartridge 204 may be removable from the body portion 208. The body portion 208 may have an actuation button 210 or other component configured to both extend a needle from the device 202 and dispense a solution from the device 202. This may alternatively be referred to as insertion of a needle into the user and injection of the solution into the user.

A safety mechanism or assembly, described more fully below, may prevent injection unless/until proper positioning and/or pressure are applied to the injection device. Upon proper positioning and pressure, the injection device may be configured to insert a needle from within the cartridge into a user and, upon full insertion of the needle, inject the solution stored in the cartridge into the user. The cartridge may then be removed from the body portion 208, preparing the body portion 208 for engagement with another cartridge.

The injection device 202 may have a multi stage deployment. Actuation of the actuation button leads to insertion of the needle. Upon complete insertion of the needle, the solution may be injected. In various embodiments, the solution comprises a medication such as botulinum toxin. While deployment is two stage, activation is may be achieved by a single user action, for example, depression of actuation button 210. In alternative embodiments, two stage user activation may be employed. Further, in some embodiments, a safety mechanism is released prior to insertion of the needle.

More particularly, in one embodiment, an actuation button will not work until a needle shield is fully depressed, for example by pushing the needle shield against a patient's skin at an injection site. De-activation of the actuation button may be done in any suitable manner. In one embodiment, the actuation button may not be actuated until the needle shield is fully depressed. In another embodiment, the actuation button may not trigger insertion of the needle until the needle shield is fully depressed. Once the needle shield is fully depressed, the actuation button may be pressed and a two stage injection occurs. The first is insertion of the needle, for example via a spring force. The second stage, which occurs upon full insertion of the needle, is injection of a solution through the needle.

The body portion 208 of the injection device may be configured and/or sized for a comfortable fit in a human hand and, as such, may be sized, shaped, or molded in the general form of a baton, stick, handle, or other relatively comfortable shape for grasping by the human hand. In one or more embodiments, the body portion 208 may generally have an elongated pen-like length and size. In one embodiment, the body portion 208 may have a generally circular cross sectional shape. In other embodiments, the body portion 208 may have any suitable cross section. The body portion 208 may include one or more ergonomic features.

Figure 5A:
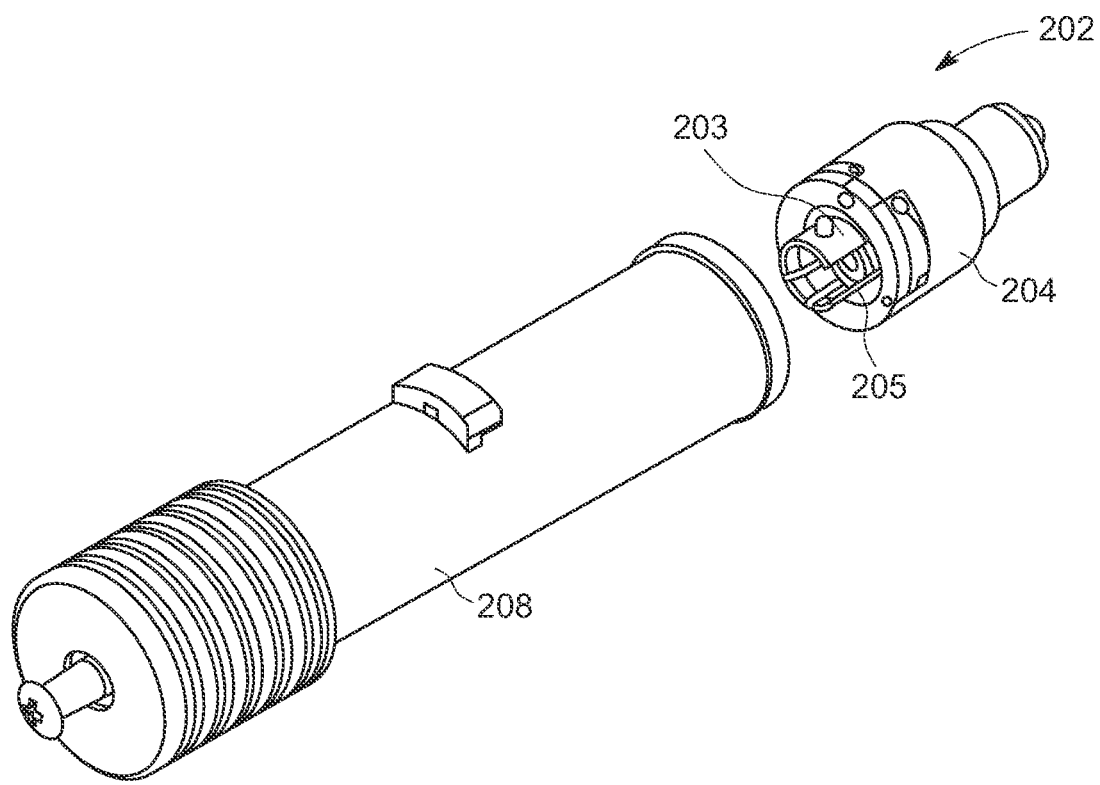
Figure 5B:
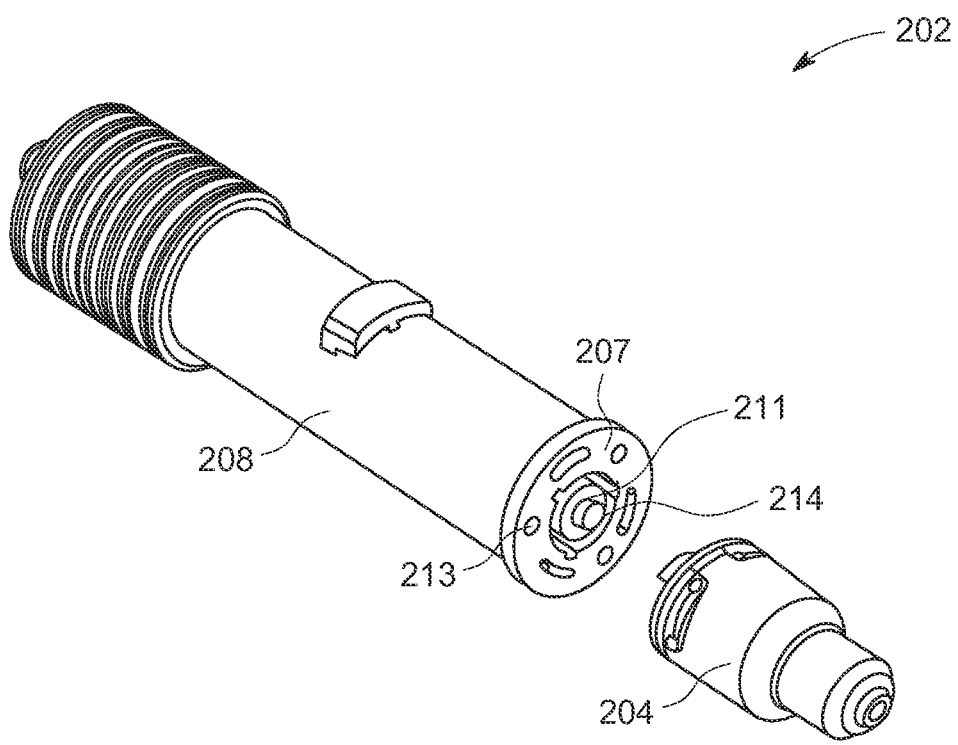

FIGS. 5a and 5b illustrate the injection device 202 with the cartridge 204 disengaged from the body portion 208, in accordance with one embodiment. The cartridge 204 includes an extension piece 203 having engagement nubs 205. The body portion 208 has a plate 207. The plate 207 includes an opening piece 214 for receiving and axially aligning with the extension piece 203. The opening piece 214 has a track 211 for the engagement nubs 205 to follow. Bumpers 213 may be provided on the plate 207 of the body portion 208 and/or on the cartridge 204 to reduce tolerance variation of the engagement of the body portion 208 with the cartridge 204. While a specific engagement of the cartridge 204 with the body portion 208 is described, it is to be appreciated that other manners of engaging the cartridge 204 with the body portion 208 may alternatively be used consistent with the teachings herein.

In the embodiment shown, to assemble the injection device 202, the extension piece 203 of the cartridge 204 is inserted into the opening piece 214 of the body portion 208. The cartridge 204 and/or body portion 208 are rotated, for example with a ¼ turn rotation, to latch the cylinder 204 to the body portion 208. This may be referred to as ¼ turn attachment and removal and may be enabled with high pitch threading of the track 211. Other amounts of rotation may alternatively be used. Bayonet lugs may be provided on a main body 230 of the injection device 202 (see FIG. 8) to lock the main body 230 in place. In alternative embodiments, other engagement mechanisms between the cartridge 204 and the body portion 208, such as a snap fit, may be used.

Figure 6:
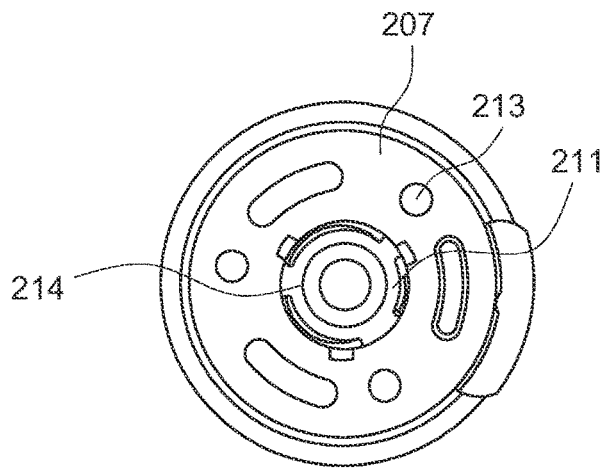

FIG. 6 illustrates an end view of the plate 207 of the body portion 208, in accordance with one embodiment. FIG. 6 shows the opening piece 214 with the track 211 for receiving the engagement nubs of the cartridge. FIG. 6 also illustrates the bumpers 213. In the embodiment shown, three bumpers are provided. In other embodiments, more or fewer bumpers, including no bumpers, may be provided.

Figure 8:
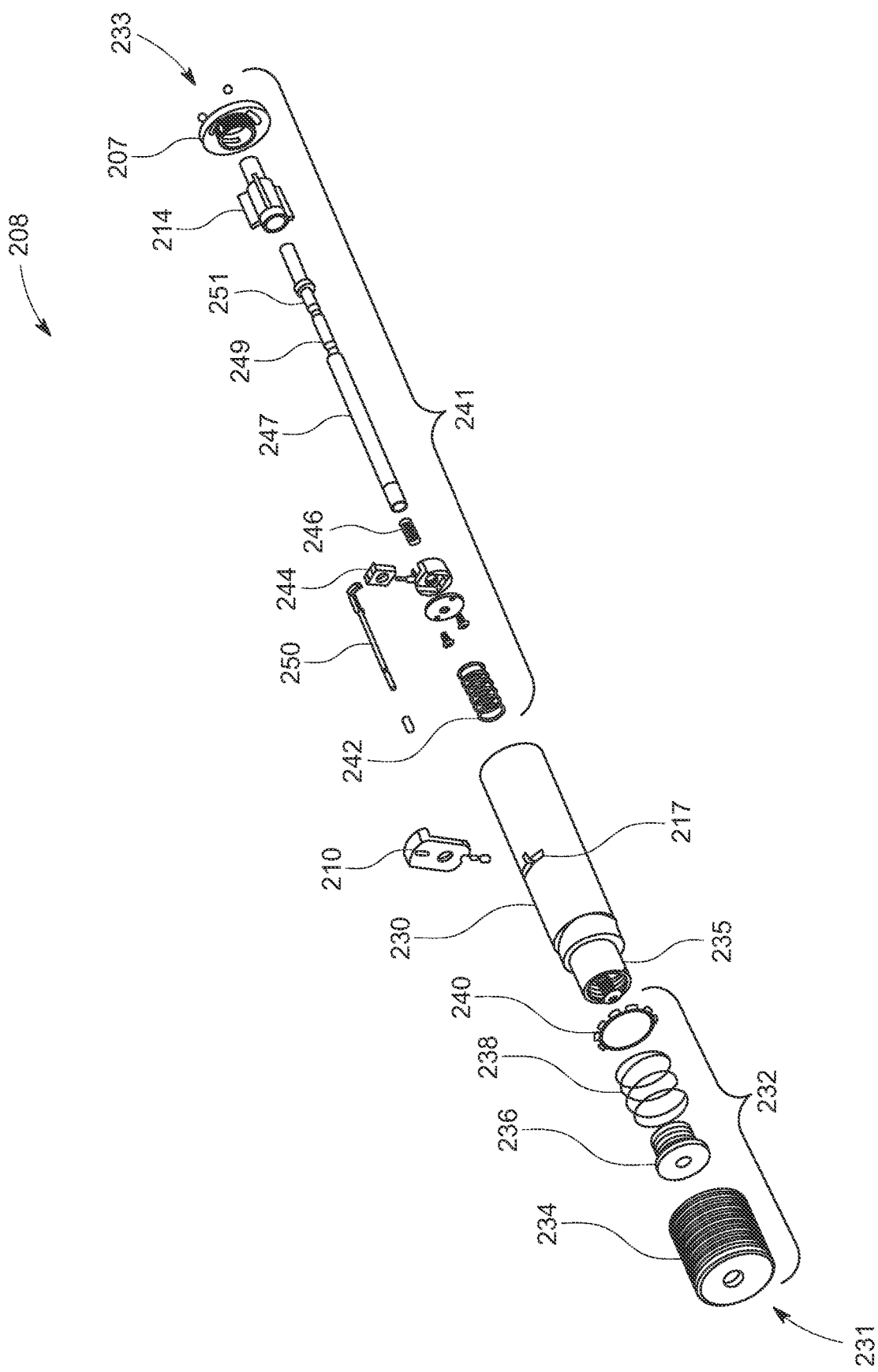

FIG. 8 illustrates an exploded view of the body portion 208 of the injection device 202, in accordance with one embodiment. In other embodiments, some of body portion 208 may vary from the embodiment shown. As shown, the body portion 208 may include a main body 230, a cocking assembly 232, and an injection assembly 241.

The main body 230 extends between a handle end 231 and a cartridge end 233. The actuation button 210 is provided on main body 230 through a slot 217. The actuation button 210 is received by a notch 249 of a main shaft 247 of the injection assembly 241, described below.

The cocking assembly 232 is provided at the handle end 231 of the injection device. The cocking assembly comprises a cocking handle 234, an end cap 236, a cocking spring 238, and a snap ring 240. As assembled, the cocking assembly sits over and in end portion 235 of main body 230. These components engage one another to enable a user to pull back on the cocking handle 234 and put the injection device 202 in a cocked position for firing, described with respect to FIGS. 11a and 11b.

The injection assembly 241 extends through the main body 230 to the cartridge end 233 and effects insertion of the needle and ejection of the medication. The injection assembly 241 includes a needle insertion spring 242, a delivery button 244, a drug delivery spring 246, a main shaft 247, the opening piece 214, and the plate 207. The delivery button 244 is received by a notch 251 on the main shaft 247. The injection assembly 241 further includes a safety interlock 250. When engaged, the safety interlock 250 prevents the actuation button 210 and delivery button 244 from being released from notches 249 and 251 of the main shaft 247, respectively. Other forms of safety interlock may alternatively be used.

Figure 9:
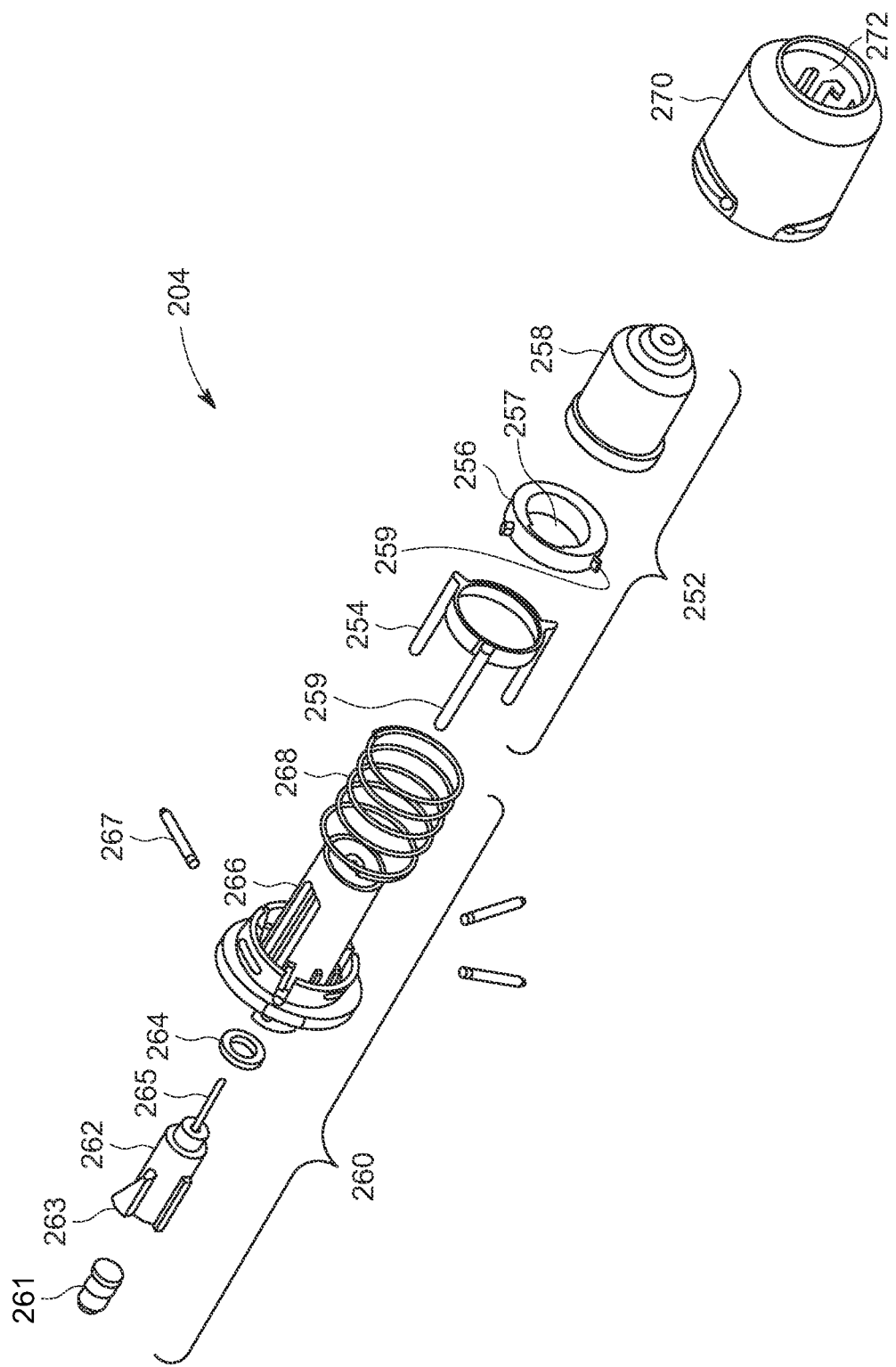

FIG. 9 illustrates an exploded view of the cartridge 204 of the injection device 202, in accordance with one embodiment. The cartridge 204 may be a single use prefilled cartridge. In general, the cartridge may be formed from any suitable material(s). In some embodiments, the cartridge is formed plastic, cyclic olefin polymer, glass, or other materials. In some embodiments, the cartridge may comprise a plurality of materials. In other embodiments, at least the solution contacting interior portion of the cartridge may be formed from glass or other material having limited or no reactivity with the to be contained solution, in order to increase shelf life of the solution stored in the cartridge. Such glass may comprise pyrex, tempered glass, or other. In some embodiments, the interior of the cartridge thus may comprise glass or other non-reactive material and such interior may be encased with a moldable or formable material such as plastic, wherein the moldable material is shaped as illustrated in the figures.

The cartridge 204 may include a syringe assembly 260, a safety assembly 252, and an outer housing 270.

In the embodiment shown, the syringe assembly 260 includes a plunger 261, a syringe 262 having fins 263 and a needle 265, an o-ring 264, a syringe holder 266, roll pins 267, and a spring 268. The roll pins 267 are retained in the syringe holder 266. A drug chamber (see FIGS. 13a and 13b) is provided within the syringe 262. In some embodiments, the drug chamber may be formed of a different material than the rest of the cartridge. For example, the drug chamber may be formed from a generally non-reactive material such as glass or cyclic olefin polymer, and other portions of the cartridge may be formed of a moldable or formable material such as plastic.

The drug chamber may be configured for holding an injectable fluid, drug, solution, or substance for dispensing from the injection device. The plunger 261 is positioned to poise the solution for injection. The drug chamber may be fluid communication with the needle 265. The plunger 261 may be configured to move through the drug chamber when engaged by the main shaft of the body portion/handle so as to cause the solution in the drug chamber to be dispensed from the drug chamber through the needle 265. It is to be appreciated that different needle lengths may be used for different injection sites or treatments. In some embodiments, the needle may have a length of between about 5 mm and about 10 mm and an insertion length of between about 3 mm and about 6 mm. In one embodiment, the needle has a length of 7.89 mm and an insertion length of 4 mm. In general, any suitable length, insertion length, or diameter of needle may be used.

In some embodiments, the injection device 202 may have an insertion length or needle depth setting or component. For example, the respective device may have a threaded component arranged on an end through which the needle may extend. The threaded component may be turned in one direction to lengthen the body of the injection device or cartridge, and in another direction to shorten the body of the injection device or cartridge. In this way, the threaded component may be configured to control a length of needle that extends from the injection device during an injection. Thus, the depth of the injection may be at least partially controlled by use of the threaded component. In other embodiments, the needle depth component may lengthen and shorten using different means, other than threading. In some embodiments, the needle depth component or setting may be adjustable by a user. In other embodiments, the needle depth component or setting may be a permanent or semi-permanent adjustment or setting, which may be preconfigured prior to the user's receipt of the kit. In some embodiments, a permanent, semi-permanent, or temporary needle depth setting may be configured such that a needle may extend no more than $\frac{1}{8}^{th}$ of an inch beyond the injection device, for example. In other embodiments, the needle depth setting may be configured for a longer or shorter needle depth. For example, for use with vaccinations or other intramuscular administration, the needle or injection depth may be on the order or 1 to 1.5 inches.

The safety assembly 252 may include a safety interlock 254 having pins 259, a slip ring 256 having notches 257 and posts 255, and a needle shield 258. The needle shield secludes the needle unless or until it is pressed against the skin. The needle shield includes an opening to allow the needle to extend therethrough to penetrate the skin. When the cartridge is pressed against the skin, the needle may approach the end of the opening or it may stay stationary until the main shaft advances the needle into the skin.

Figure 7A:
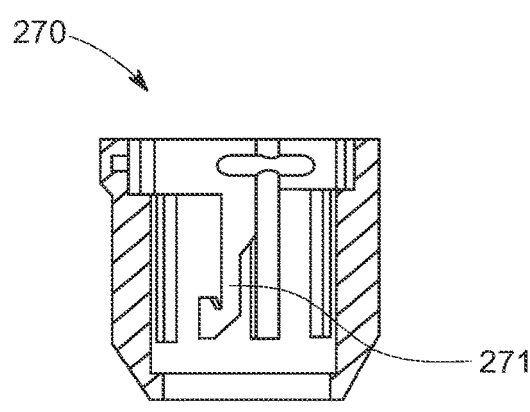
Figure 7B:
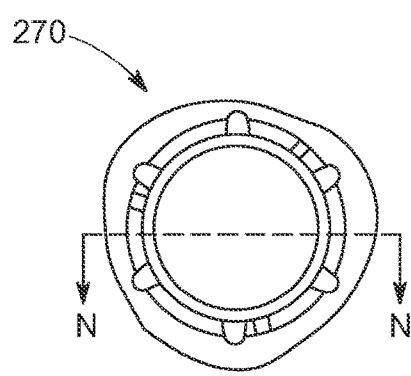
Figure 10A:
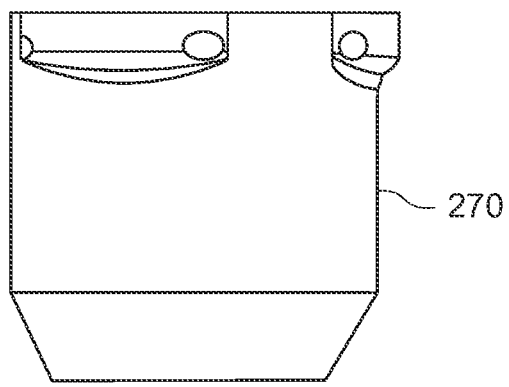
Figure 10B:
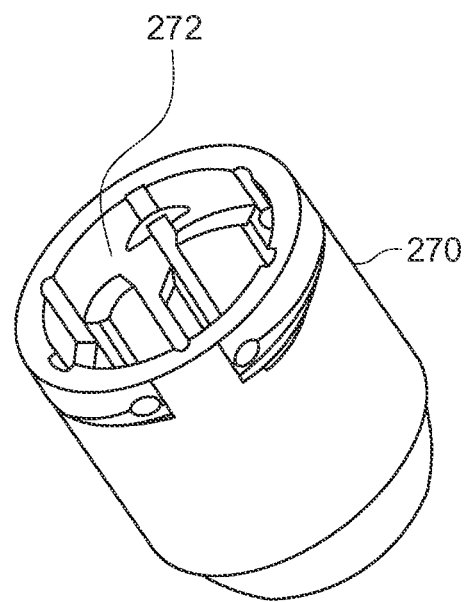

FIG. 7a illustrates a cross section of the outer housing 270 of the cartridge 204, in accordance with one embodiment. FIG. 7b illustrates an end view of the outer housing of the cartridge 204, in accordance with one embodiment. FIGS. 10a and 10b illustrate alternative views of the outer housing of FIGS. 7a and 7b. As shown, the outer housing 270 includes tracks 272 on an interior surface for receiving the slip ring 256 of the safety assembly 252. Once the unit is activated, fins 263 of the syringe 262 rotate the slip ring 256. The slip ring 256 travels down the tracks 272 and is then locked forward and is unable to rest to an initial position. This locks the needle shield 258 forward so the cartridge 204 cannot be used a second time. Accordingly, a safety interlock wherein when the safety interlock is in a used configuration, the needle shield is locked in a forward position and the cartridge cannot be reused Use In one embodiment, to use the injection device and inject the solution or medication, a user cocks the body portion/handle 208, attaches a cartridge 204 to the body portion/handle 208, positions the injection device 202, and presses the actuation button 210.

FIGS. 11a-12b illustrate the body portion/handle 208 in the positions through which it moves during use of the injection device. FIGS. 13a-16b illustrate the cartridge 204 in the positions through which it moves during use of the injection device. FIGS. 17a-20b illustrate the injection device 202, including the body portion/handle 208 and the cartridge 204, in the positions through which it moves during use.

Figure 11A:
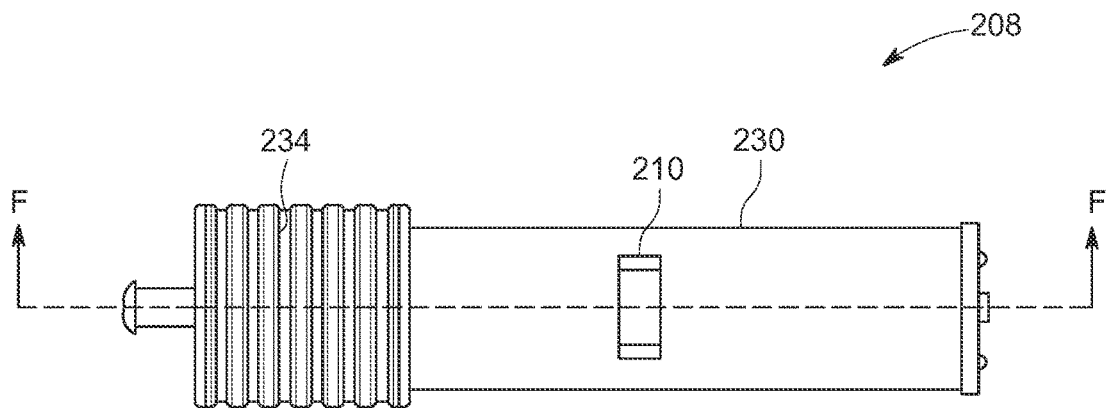
Figure 11B:
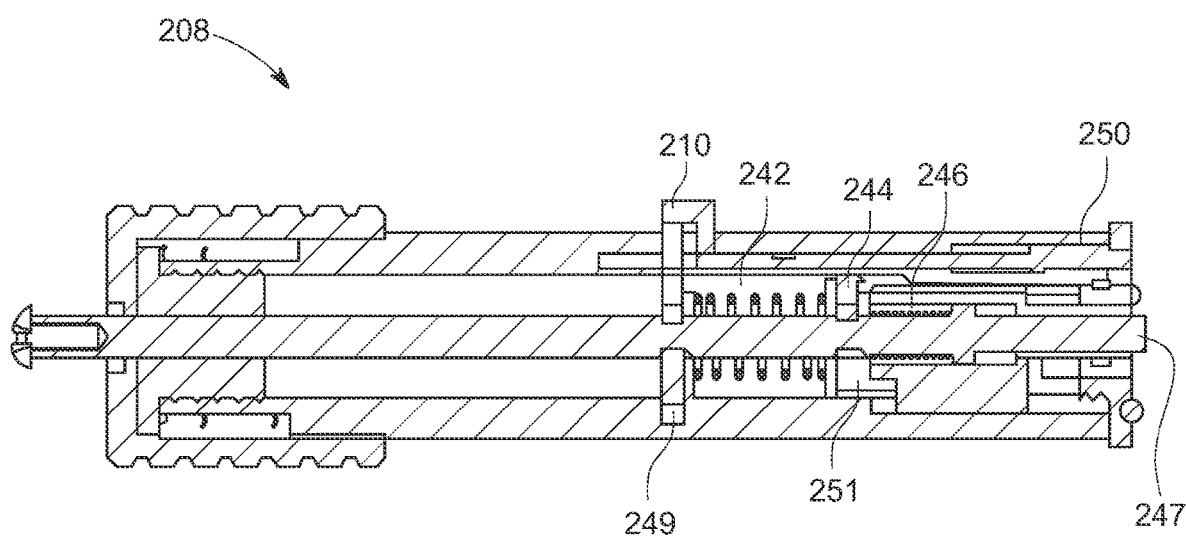

FIGS. 11a and 11b illustrate the body portion/handle 208 in the cocked position. FIG. 11a illustrates the exterior of the body portion/handle 208 as a user would perceive it. FIG.

11b illustrates a cross sectional view along Section F-F of FIG. 11a. This thus illustrates the interior of the body portion/handle 208 along Section F-F. It is to be appreciated that the position shown, the cocked position, is the position in which the body portion/handle 208 is arranged for receipt of a cartridge.

In one embodiment, in order to cock the body portion/handle 208, the user pulls back the cocking handle 234, causing the insertion spring 242 to compress behind the main shaft 247. In this position, the actuation button 210 has not been depressed and the needle insertion spring 242 is in a coiled position. Similarly, the delivery button 244 has not been actuated and the drug delivery spring 246 is in a coiled position. The actuation button 210 is engaged with notch 249 and the delivery button 244 is engaged with notch 251. The actuation button 210 maintains the main shaft 247 back and in an undeployed position. The safety interlock 250 is engaged and prevents the actuation button 210 and delivery button 244 from being released.

Figure 12A:
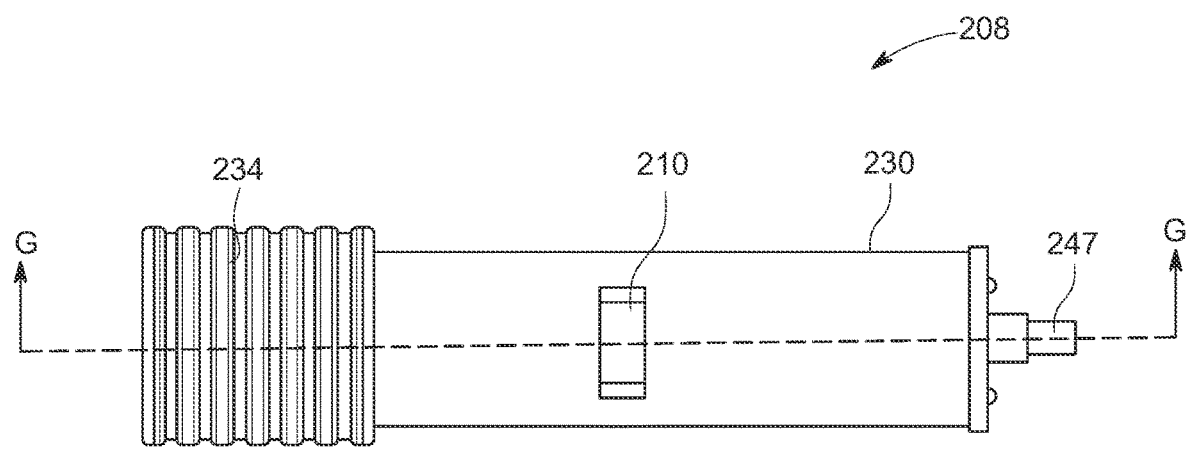
FIG. 12a illustrates the exterior of body portion/handle in the fired position, in accordance with one embodiment.
Figure 12B:
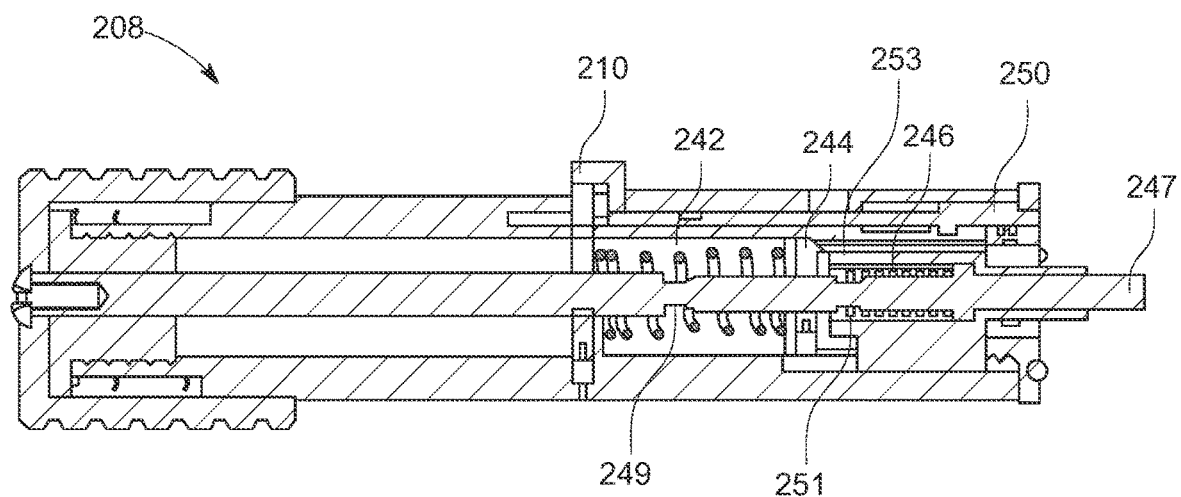
FIG. 12b illustrates the interior of the body portion/handle of FIG. 12a along Section G-G.

FIGS. 12a and 12b illustrate the body portion/handle 208 in the fired position. FIG. 12a illustrates the exterior of the body portion/handle 208 as a user would perceive it. FIG. 12b illustrates the interior of the body portion/handle 208 along Section G-G of FIG. 12a. It is to be appreciated that the position shown, the fired position, is the position in which the body portion/handle 208 is arranged after medication has been dispensed from the device.

In one embodiment, in order to fire the injection device, the user presses the actuation button 210. This releases the actuation button 210 from the notch 249 in the main shaft 247, releasing the injection button's hold on the main shaft 247. Pressing of the actuation button 210 from the main shaft 247 will nevertheless not result in firing of the device unless the safety interlock 250 is disengaged. This is done when a cartridge is fixed to the body portion/handle 208 and pressed against a surface, such as the skin of a user, to depress the needle shield of the cartridge. Assuming the safety interlock 250 is disengaged, release of the main shaft 247 inserts the needle into the patient via delivery button 244. At the full travel of main shaft 247 and delivery button 244, the second stage occurs. The final linear movement causes the ramp 253 inside housing 230 to actuate the delivery button 244 and release the delivery button 244 from the notch 251 which will then inject the solution into the patient (shaft 247 pushes on plunger 261).

Accordingly, in this position, the actuation button 210 has been depressed and the needle insertion spring 242 is in a released position. Similarly, the delivery button 244 has been actuated and the drug delivery spring 246 is in a released position. The actuation button 210 is disengaged from notch 249 and the delivery button 244 is disengaged from notch 251.

Figure 13A:
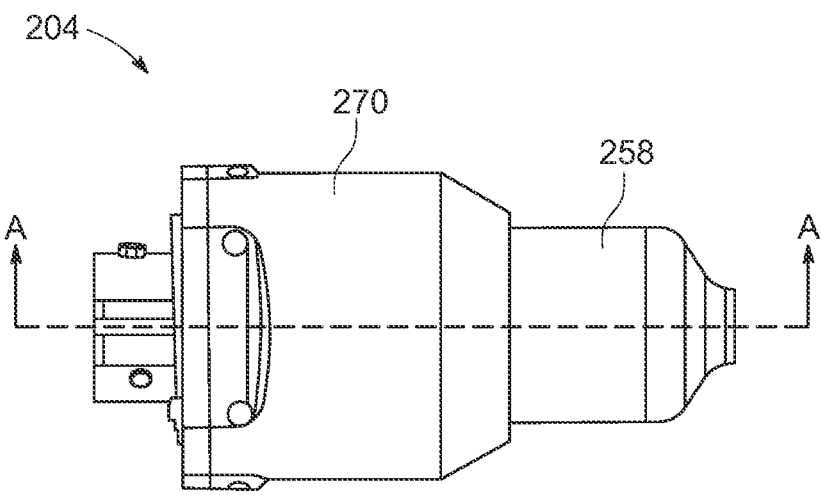
FIG. 13a illustrates the exterior of a fresh cartridge before fixation on a body portion/handle and before use, in accordance with one embodiment.
Figure 13B:
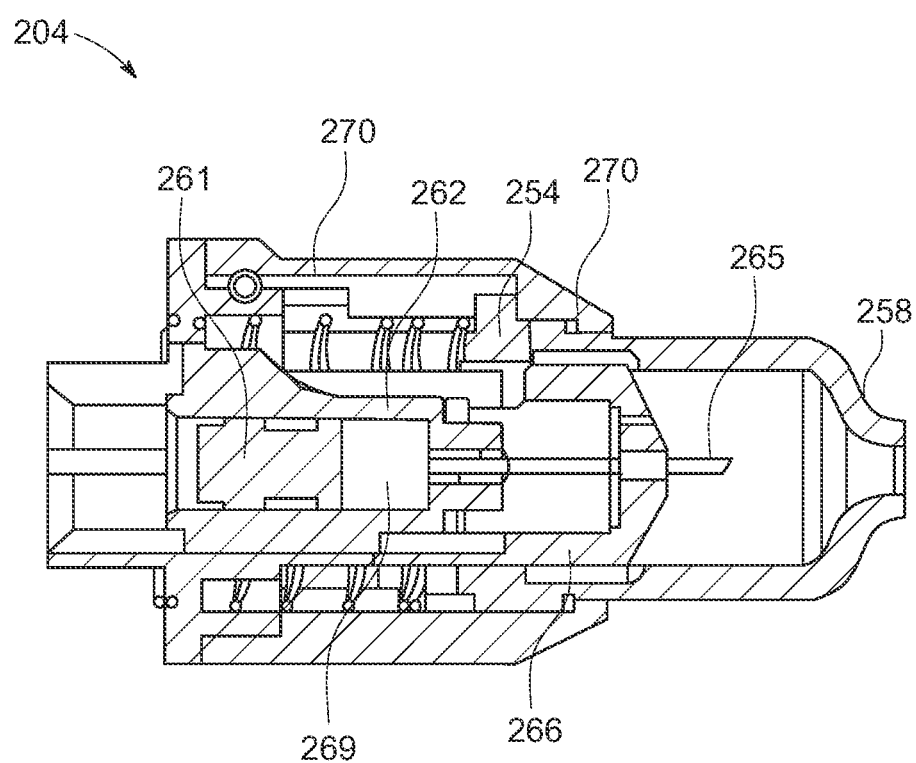
FIG. 13b illustrates the interior of the cartridge of FIG. 13a along Section A-A.

FIGS. 13a and 13b illustrate a fresh cartridge 204 before fixation on a body portion/handle and before use. FIG. 13a illustrates the exterior of the cartridge 204 as a user would perceive it. FIG. 13b illustrates the interior of the cartridge 204 along Section A-A of FIG. 13a.

In an unused and unfixed position, the syringe 262 is in the syringe holder 266 and set back from a needle end of the syringe holder 266. the plunger 261 is engaged with the syringe 262 but is not pressing fluid in the drug chamber 269. The needle shield 258 extends over and away from the needle 265. Movement of the plunger 261 and needle 265 is effectuated by the main shaft 247 of the body portion/handle (see, for example, FIG. 8).

Figure 14A:
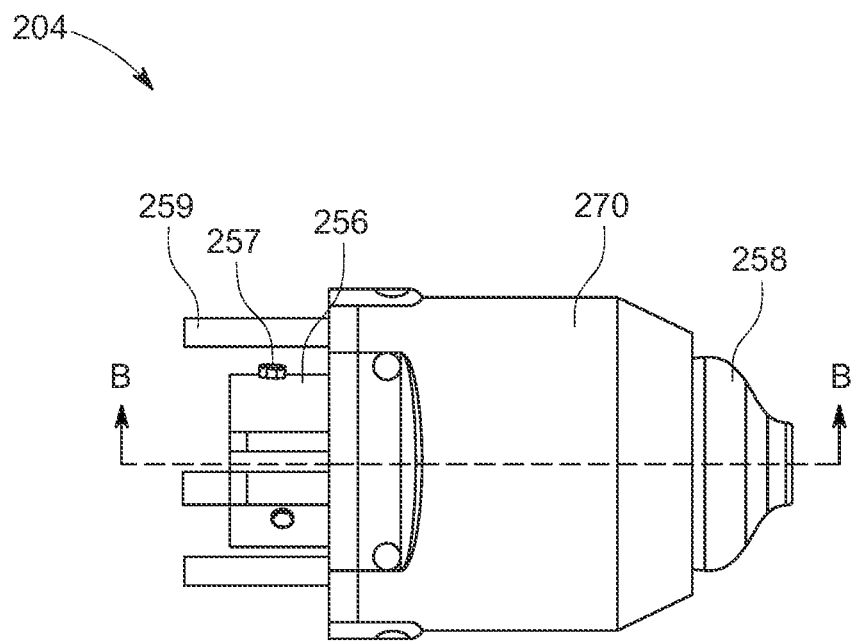
FIG. 14a illustrates the exterior of a fresh cartridge as fixed to the body portion/handle with the needle shield depressed, in accordance with one embodiment.
Figure 14B:
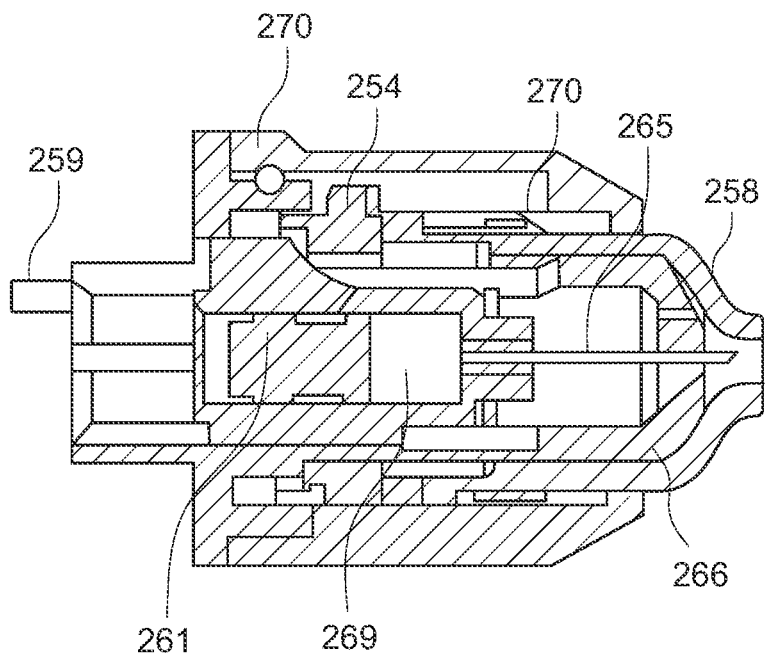
FIG. 14b illustrates the interior of the cartridge of FIG. 14a along Section B-B.

FIGS. 14a and 14b illustrate a fresh cartridge 204, as it would present when fixed to the body portion/handle, and with the needle shield depressed. FIG. 14a illustrates the exterior of the cartridge 204 as a user would perceive it. FIG. 14b illustrates a cross section of the cartridge 204 along Section B-B of FIG. 14a, thus illustrating the interior of the cartridge. It is to be appreciated that in the position shown, the cartridge 204 will have released the safety mechanism on the body portion/handle. In general, the needle shield 258 is depressed (thereby releasing the safety mechanism) when the injection device is pressed against the skin by a user. In some embodiments, the force used to depress the needle shield may range from about 0.5 pounds to about 4.5 pounds. In one embodiment, the force used to depress the needle shield is less than about 1 pound.

As shown, the needle shield 258 is depressed. This causes the needle shield 258 to engage the safety interlock 254 of the cartridge 204 and press back pins 259. The pins 259 in turn press on the safety interlock 250 of the body portion/handle 208. While this releases the safety mechanism of the body portion/handle 208, the needle 265 remains in the retracted position with syringe 268 set back in the syringe holder 266 and the needle shield 258 extending over the needle 265 until the user presses actuation button 210. The plunger 261 is engaged with the syringe 262 but still is not pressing fluid in the drug chamber 269.

Figure 15A:
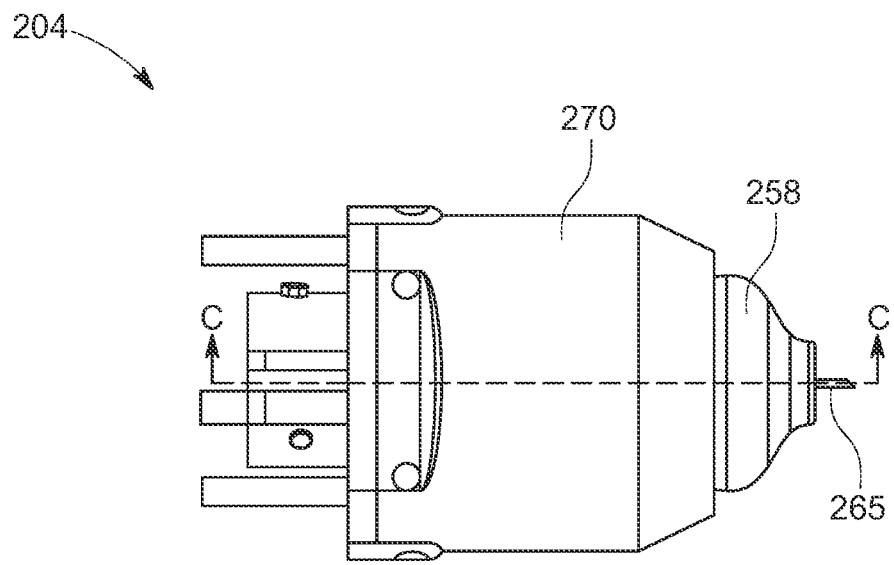
FIG. 15a illustrates the exterior a cartridge as fixed to the body portion/handle with the needle inserted and the drug dispensed, in accordance with one embodiment.
Figure 15B:
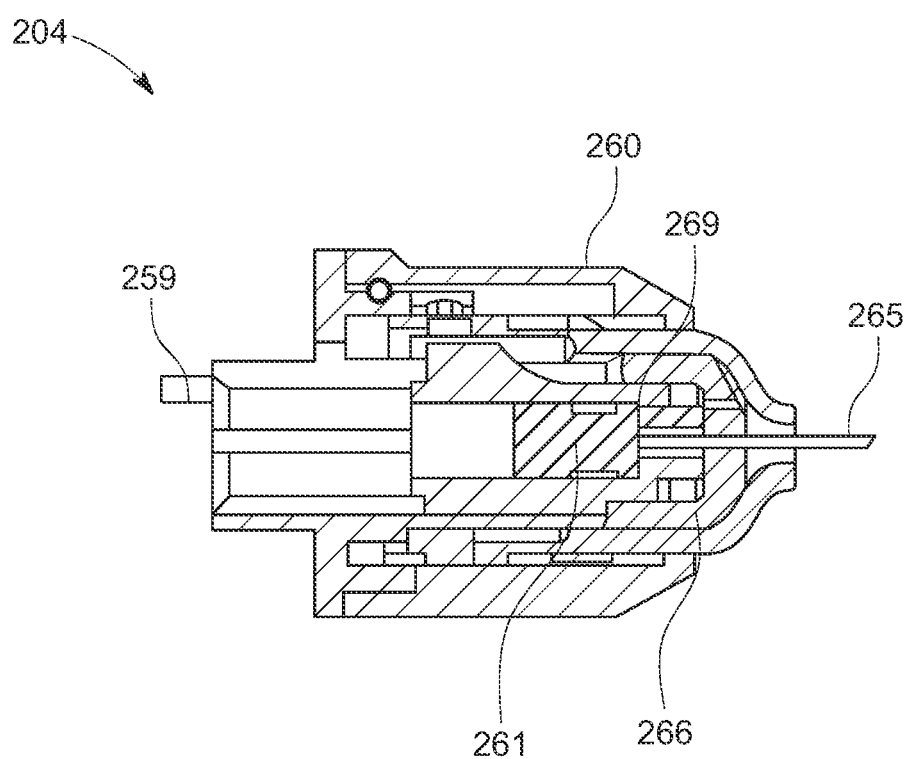
FIG. 15b illustrates the interior of the cartridge of FIG. 15a 204 along Section C-C.

FIGS. 15a and 15b illustrate a cartridge 204, as it would present when fixed to the body portion/handle with the needle inserted and the drug dispensed. FIG. 15a illustrates the exterior of the cartridge 204 as a user would perceive it. FIG. 15b illustrates a cross section of the cartridge 204 along Section C-C of FIG. 15a, thus illustrating an interior of the cartridge 204. It is to be appreciated that in the position shown, the cartridge 204 is pressed against a user and the needle is inserted into the user.

As shown, the needle shield 258 is depressed and positioned substantially as in the position of FIGS. 14a and 14b. In the position of FIGS. 15a and 15b, however the plunger 261 is engaged with the syringe 262 and has pushed the syringe 268 forward in the syringe holder 266 to force the needle 265 out of the outer housing 270 and into an insertion position. In one embodiment, the main shaft 247 pushes the back end of the syringe to insert the needle 265 into the patient. Once the second stage occurs and the delivery button 244 is released, the main shaft 247 pushes the plunger 261 to inject the pharmaceuticals. In some embodiments, the needle 265 extends from the cartridge an insertion length of between about 3 mm and about 6 mm. Movement of the plunger 261 further acts to force fluid from the drug chamber 269 through the needle 265. In some embodiments, the needle 265 may extend from the outer housing at a distance of between about 2 mm and about 6 mm. It is to be appreciated that the extension of the needle 265 from the housing, or the injection length or insertion depth, may vary and may depend on what is being injected where.

Figure 16A:
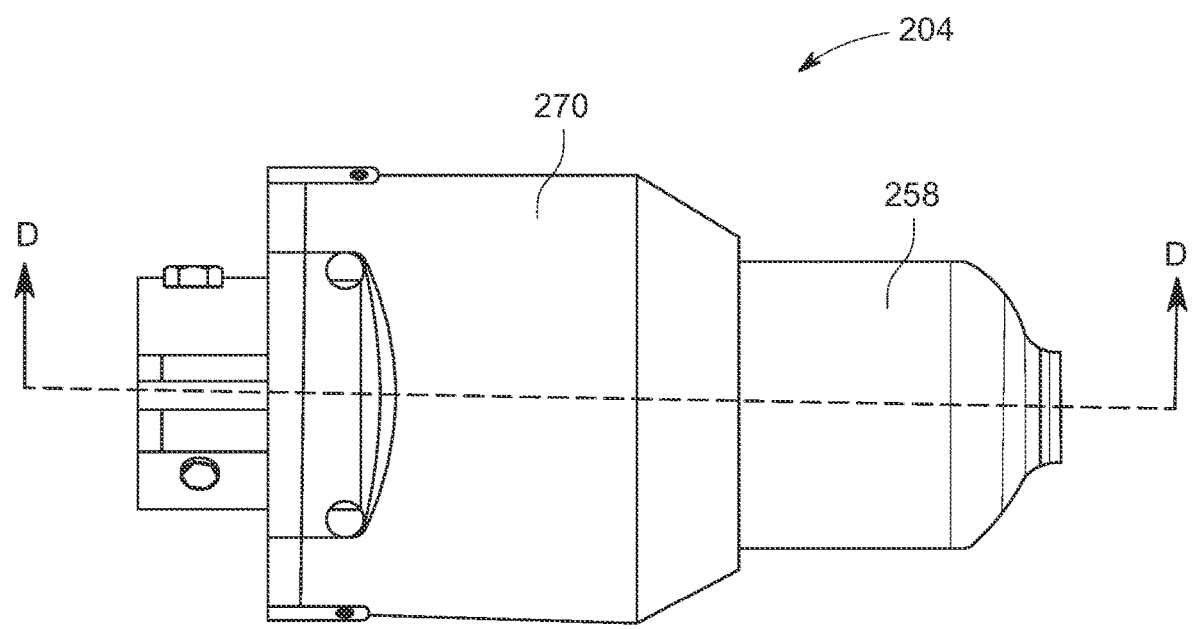
FIG. 16a illustrates the exterior of a spent cartridge, with the drug dispensed and the needle shield locked in a forward position, in accordance with one embodiment.
Figure 16B:
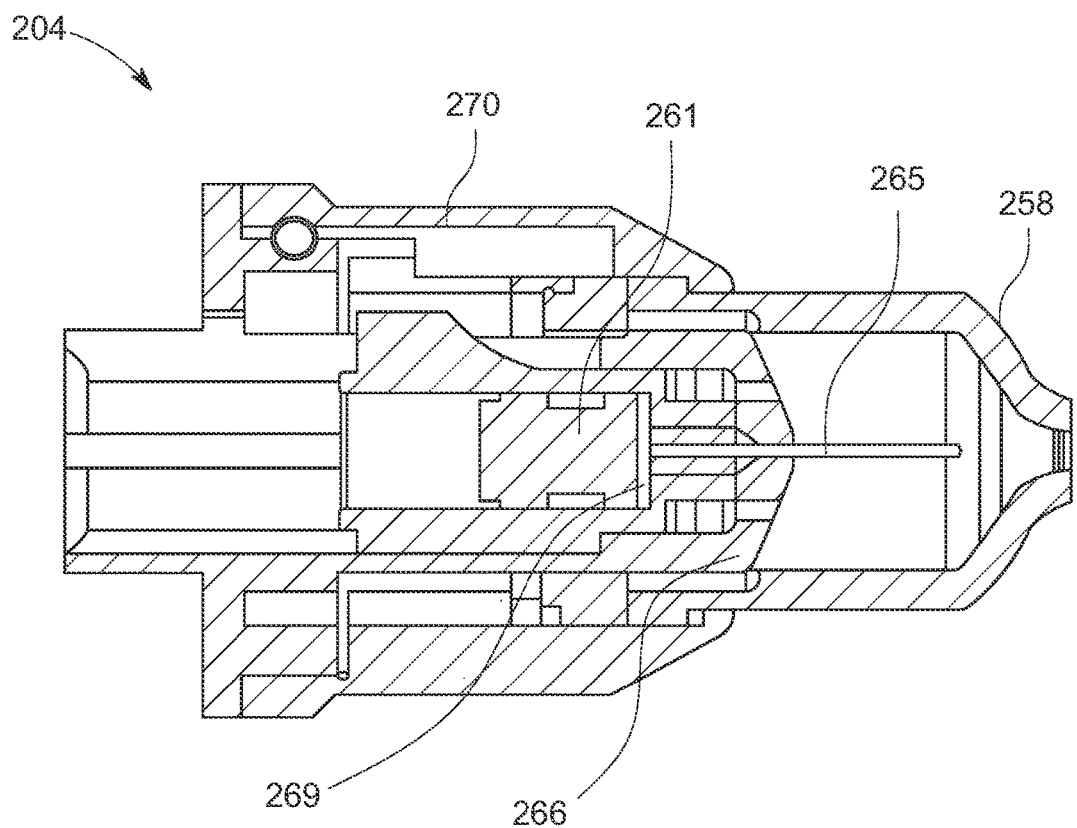
FIG. 16b illustrates the interior of the cartridge of FIG. 16a along Section D-D.

FIGS. 16a and 16b illustrate a spent cartridge 204, with the drug dispensed and the needle shield 258 locked in a forward position. FIG. 16a illustrates the exterior of the cartridge 204 as a user would perceive it. FIG. 16b illustrates a cross-section of cartridge 204 along Section D-D of FIG. 16a, thereby illustrating the interior of the cartridge 204. It is to be appreciated that in the position shown, the cartridge 204 has been lifted from the user and the needle removed from the user.

After injection of the solution or medication, a user lifts the injection device from their skin. Lifting the injection device pulls the needle from the user and releases the force being put on the needle shield 258. The needle shield 258 thus returns to its initial position, shown in FIGS. 13a and 13*b*, and is locked in place. Initially, the posts 259 of the slip ring 256 of the safety assembly 252 of the cartridge 204 can go back and forth in the tracks 272 of the outer housing 270. The notches 257 of the slip ring 256 receive the fins 263 of the syringe 262. The fins 263 rotate the slip ring 256. Once the actuation button 210 is pressed, the fins 263 of the syringe 260 move the posts 259 laterally in the track 272. Once this happens, the needle shield 258 is pushed forward and locked into place.

Upon return of the needle shield 258 to its initial position, the pins 259 pull away from the safety interlock 250 of the body portion/handle 208 and the safety mechanism is reengaged. Notwithstanding return of the needle shield 258 to its initial position, the needle 265 remains in an insertion position—extending from the outer housing but now covered by the needle shield 258.

Figure 17A:
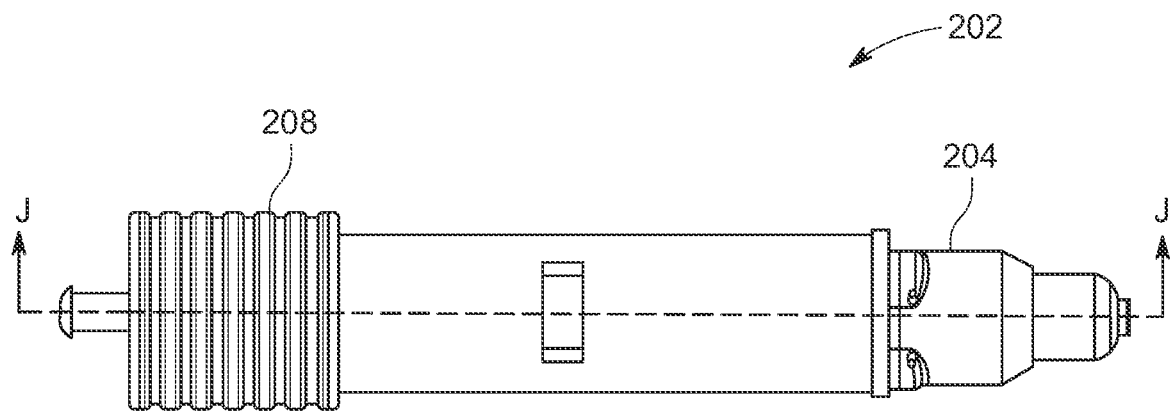
FIG. 17a illustrates an exterior of an injection device with the body portion/handle cocked and a fresh cartridge attached, in accordance with one embodiment.
Figure 17B:
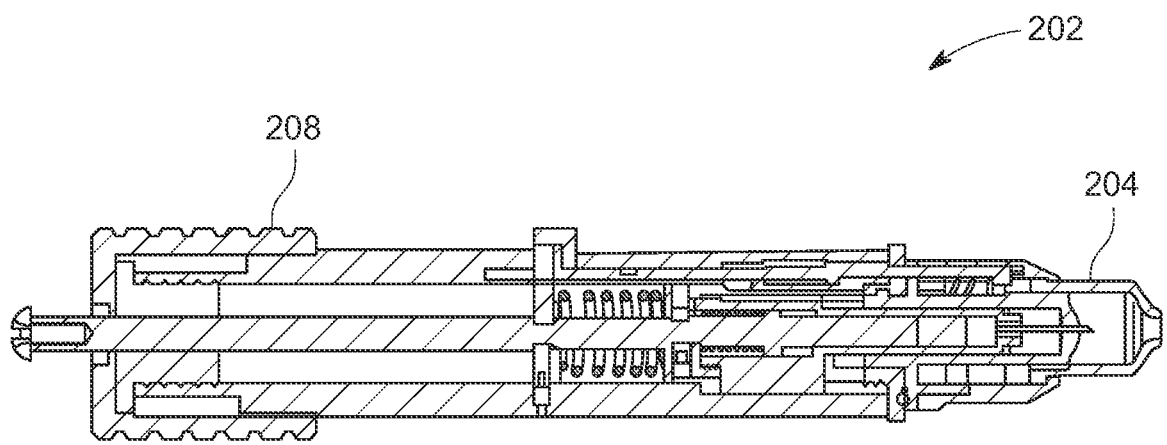
FIG. 17b illustrates the interior of the injection device of FIG. 17a along Section J-J.

FIGS. 17*a* and 17*b* illustrate the injection device 202 with the body portion/handle 208 cocked and a fresh cartridge 204 attached. FIG. 17*a* thus combines FIG. 11*a* (cocked body portion/handle 208) and FIG. 13*a* (fresh cartridge) and FIG. 17*b* combines FIGS. 11*b* and 13*b*. FIG. 17*a* illustrates the exterior of the injection device 202 as a user would perceive it. FIG. 17*b* illustrates the interior of the injection device 202 along Section J-J of FIG. 17*a*.

Figure 18A:
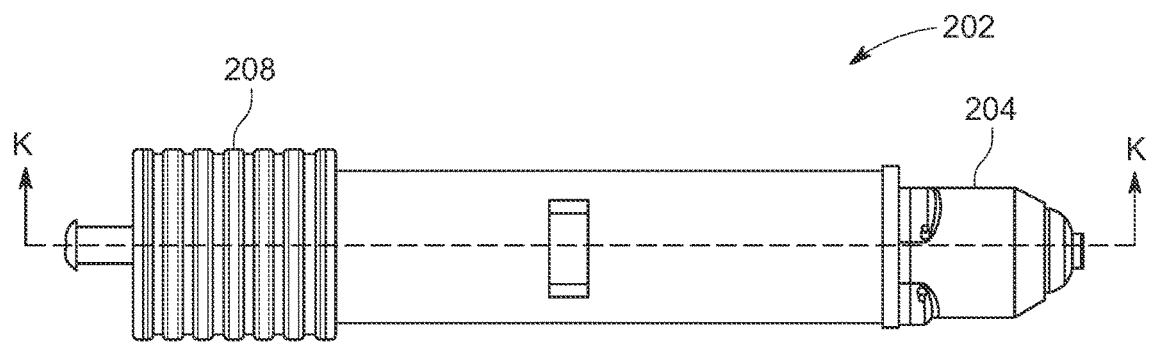
FIG. 18a illustrates the exterior of an injection device with the body portion/handle cocked and a fresh cartridge attached with the needle shield depressed, in accordance with one embodiment.
Figure 18B:
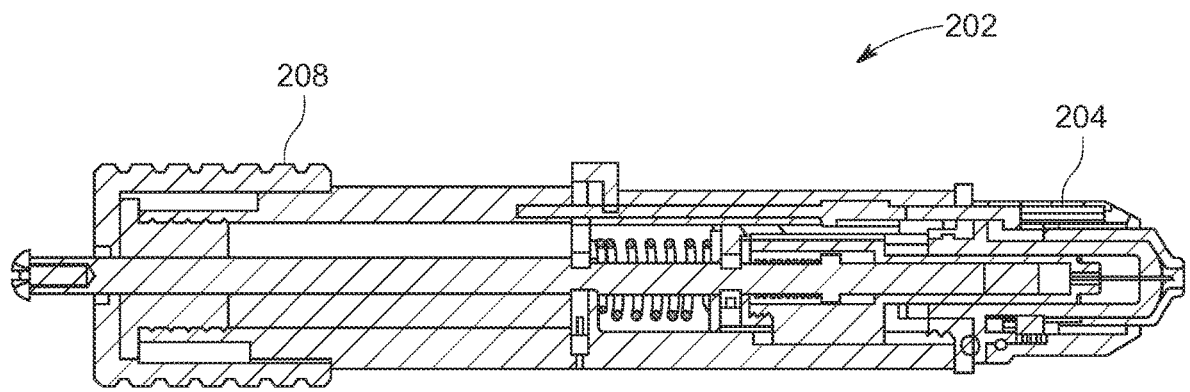
FIG. 18b illustrates the interior of the injection device of FIG. 18a along Section K-K.

FIGS. 18*a* and 18*b* illustrate the injection device 202 with the body portion/handle 208 cocked and a fresh cartridge 204 attached with the needle shield 258 depressed. FIG. 18*a* thus combines FIG. 11*a* (cocked body portion/handle 208) and FIG. 14*a* (fresh cartridge with needle shield depressed) and FIG. 18*b* combines FIGS. 11*b* and 14*b*. FIG. 18*a* illustrates the exterior of the injection device 202 as a user would perceive it. FIG. 18*b* illustrates the interior of the injection device 202 along Section K-K of FIG. 18*a*.

Figure 19A:
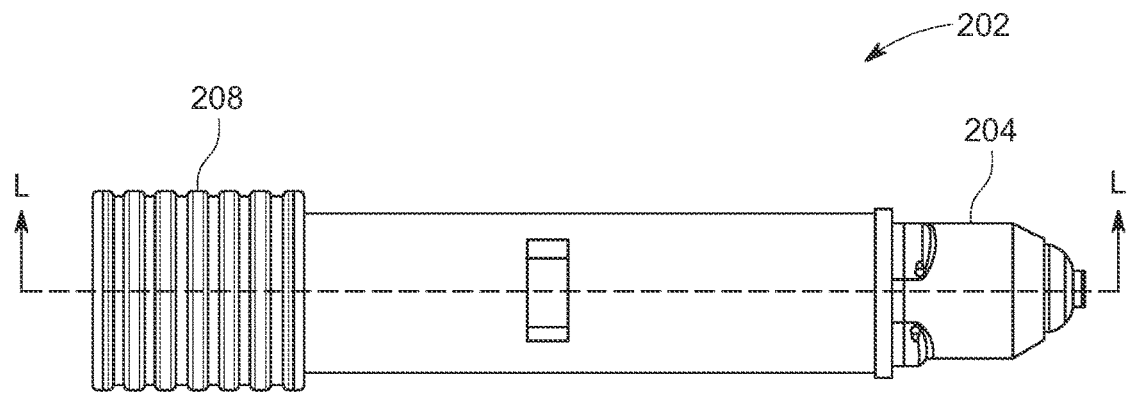
FIG. 19a illustrates the exterior of an injection device with the body portion/handle fired and a cartridge attached with the drug dispensed, in accordance with one embodiment.
Figure 19B:
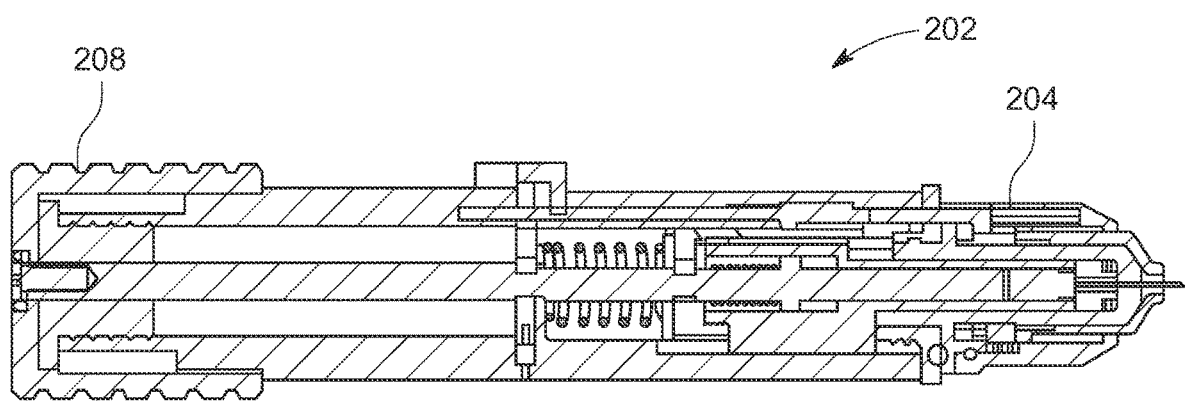
FIG. 19b illustrates the interior of the injection device of FIG. 19a along Section L-L.

FIGS. 19*a* and 19*b* illustrate the injection device 202 with the body portion/handle 208 fired and a cartridge 204 attached with the drug dispensed. FIG. 19*a* thus combines FIG. 12*a* (fired body portion/handle 208) and FIG. 15*a* (cartridge with needle inserted and drug dispensed) and FIG. 19*b* combines FIGS. 12*b* and 15*b*. FIG. 19*a* illustrates the exterior of the injection device 202 as a user would perceive it. FIG. 19*b* illustrates the interior of the injection device 202 along Section L-L of FIG. 19*a*.

Figure 20A:
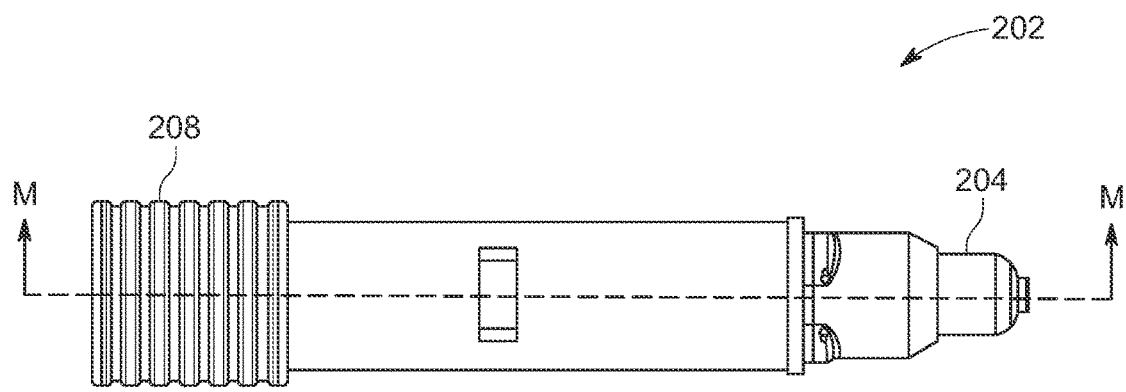
FIG. 20a illustrates the exterior of an injection device with the body portion/handle fired and a cartridge attached with the drug dispensed and the needle shield locked forward, in accordance with one embodiment.
Figure 20B:
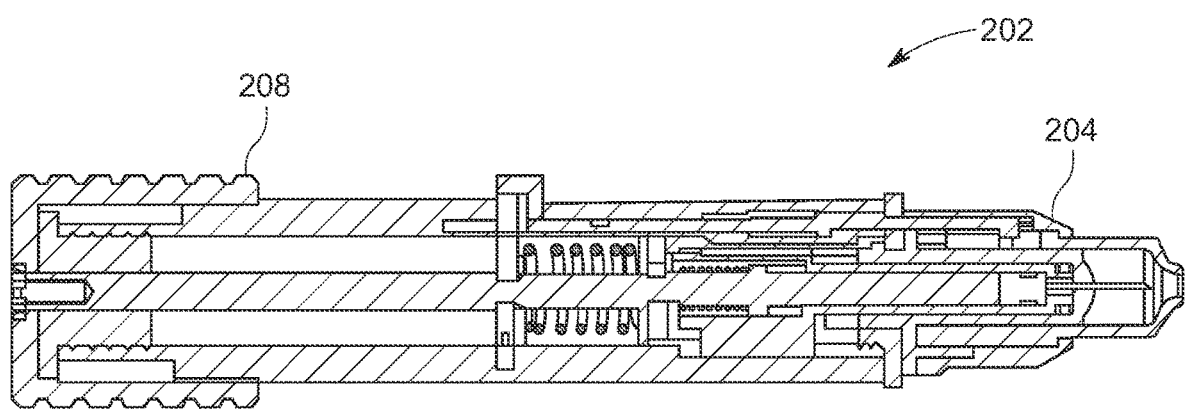
FIG. 20b illustrates the interior of the injection device of FIG. 20a along Section M-M.

FIGS. 20*a* and 20*b* illustrate the injection device 202 with the body portion/handle 208 fired and a cartridge 204 attached with the drug dispensed and the needle shield locked forward. FIG. 20*a* thus combines FIG. 12*a* (fired body portion/handle 208) and FIG. 16*a* (spent cartridge with needle shield locked forward) and FIG. 20*b* combines FIGS. 12*b* and 16*b*. FIG. 20*a* illustrates the exterior of the injection device 202 as a user would perceive it. FIG. 20*b* illustrates the interior of the injection device 202 along Section M-M of FIG. 20*a*.

The user thus starts with a body portion/handle. The user fixes a fresh cartridge to the body portion/handle by rotating the cartridge onto the body portion/handle. The user cocks the injection device by pulling back on the cocking handle. The user presses the needle shield of the cartridge against their skin, thereby releasing the safety mechanism. With the safety mechanism released, the user is able to press the actuation button, which releases the main shaft of the body portion/handle. The main shaft deploys the plunger of the cartridge, the needle is extended, and the medication is released. In some embodiments, pressing the needle shield against their skin may comprise aiming the injection device towards a template and pressing the injection device onto the template in a position such that the needle shield is positioned substantially above a marker for where injection should occur.

In the embodiment described, the safety mechanism is released by depressing the needle shield. Typically, this may occur when the user presses the tip of the cartridge against their skin just prior to injection. Broadly speaking, as the user presses the tip of the cartridge against their skin, the cartridge may engages the body portion/handle and trigger an internal mechanical or electrical switch, which allows the injection component to function. In one or more embodiments, for example, the internal switch may include a chamfered, beveled, or cam surface that causes a blocking element to cause the injection component, or main shaft, to become live. Other types of mechanical switches may also or alternatively be used such as switches that block trigger motion rather than the injection component motion. Still other approaches may also be used. Electrical switches may be used where the intruding cartridge creates or interrupts an electrical contact, which allows the injection component to become live. Still other approaches using electrical switches may be used. Moreover, the safety mechanism may be provided in any suitable location. For example, the safety mechanism may be provided entirely on the cartridge where activation of the injection component on the body portion is simply not strong enough to overcome the resistance of the safety component on the cartridge. Other approaches and locations of the safety component may alternatively be used.

In one or more embodiments, injection is generally achieved by cooperation of a main shaft of the body portion/handle and a plunger of the cartridge. The main shaft may be driven by a spring, biasing mechanism, or other advancing mechanism. The main shaft 247 and delivery button 244 push in the needle. Once delivery button 244 is released, the main shaft 247 pushes on plunger 261 to inject the solution, pharmaceutical, or medication. The needle depth may be defined by the depth at which the injection is to take place. For botulinum toxin injections, the depth may be relatively shallow, while other injections, including intramuscular injections such as vaccines, may call for deeper needle penetration. The cartridge and/or injection device may be calibrated or designed to accommodate any suitable needle penetration.

Staging Template/Tray

As discussed with respect to FIG. 3, a staging tray or template 106 may be provided. The staging tray 106 may be configured to hold the cartridges 104/204 in a position and/or arrangement for engagement by the injection device. The staging tray 106 may come preloaded with cartridges in a sterilized, sealed package. In other embodiments, the staging template may be separate from the cartridges and the cartridges may be placed in the staging template by the user.

FIG. 21 is a top view of a staging tray holding a plurality of cartridges, in accordance with one embodiment. In some embodiments, the staging tray 206 may be arranged so as to correspond with the general arrangement and order of injections. For example, as shown, the staging tray 206 may include a horseshoe or upside down U shape corresponding generally to the locations of injections extending upward/downward along the side of a left eye, across the top of the forehead, and upward/downward along the side of right eye. That is, as shown, the four left cartridges 204 may be used to perform four injections along the left eye. The five cartridges 204 arranged along the top may be used to perform injections across the forehead. The four right cartridges 204 may be used to perform four injections along the right eye. In one or more embodiments, the cartridges 204 arranged in the tray 206 may have varying doses depending on the location of the corresponding injection. As such, the template 206 may be preloaded with the cartridges to assure proper doses are used in appropriate locations. In general, the tray may be configured to generally correspond with any injection location on the body and roughly indicate where an injection should be done on the body. Alternatively, in some embodiments, the tray may not have locations corresponding with injection locations. For example, the tray may have spaces to hold cartridges wherein the spaces indicate the volume of solution in the cartridge.

Figure 21:
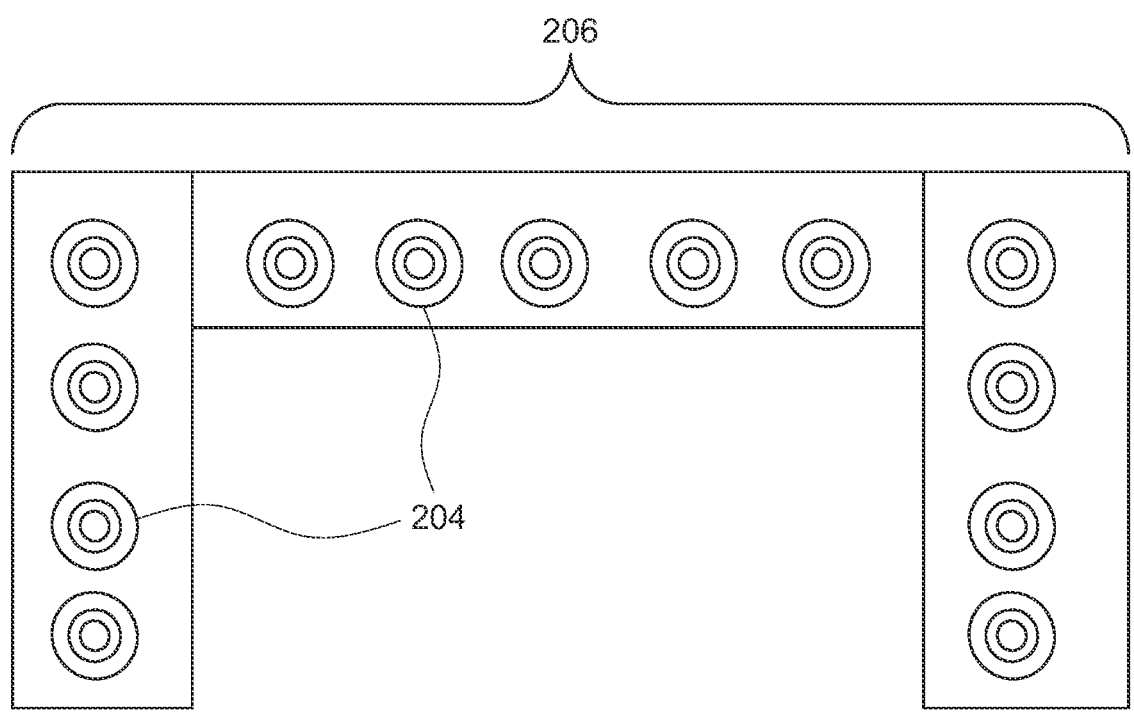
FIG. 21 illustrates a top view of a staging tray holding a plurality of cartridges, in accordance with one embodiment.

In one or more embodiments, the staging tray 206 shown in FIG. 21 may be assembled by the user. For example, while the cartridges may be preloaded into the tray, the tray may be shipped in a plurality of parts as defined by the dividing lines. The tray may be assembled by the user by place the tray on a relatively surface and placing the pieces adjacent to each other as shown. In some embodiments, the tray may include hook and loop, adhesive, or other fastening mechanisms to secure the several parts of the tray together.

Patch/Injection Template

Figure 22:
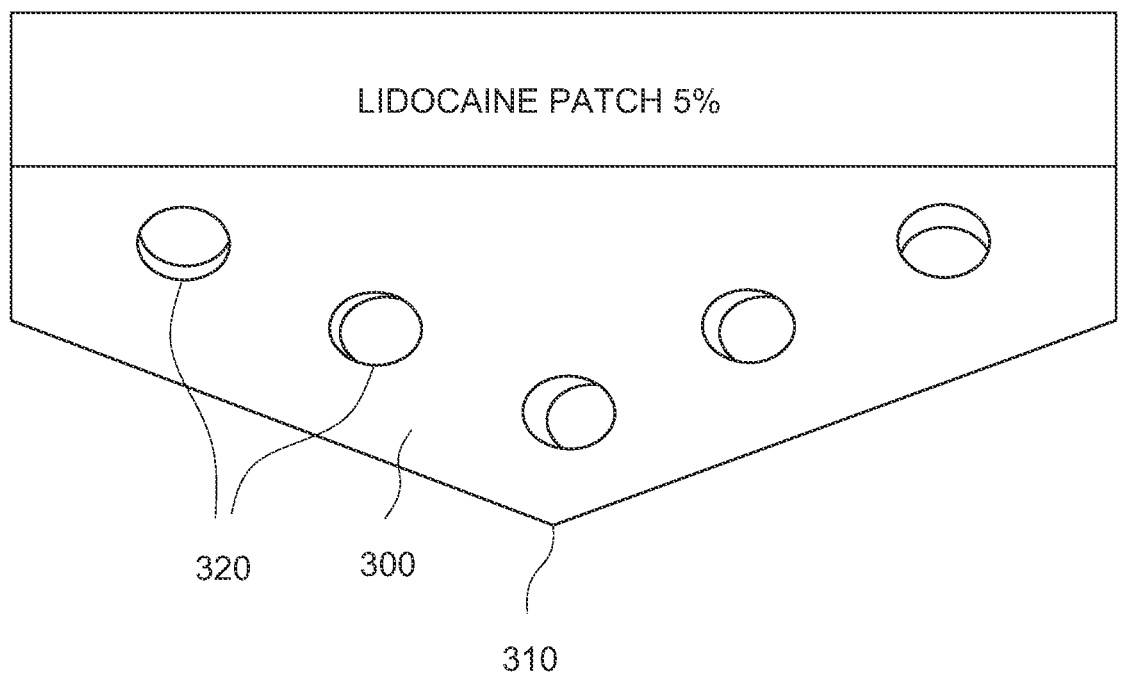
FIG. 22 illustrates a front view of an injection patch, in accordance with one embodiment.
Figure 23:
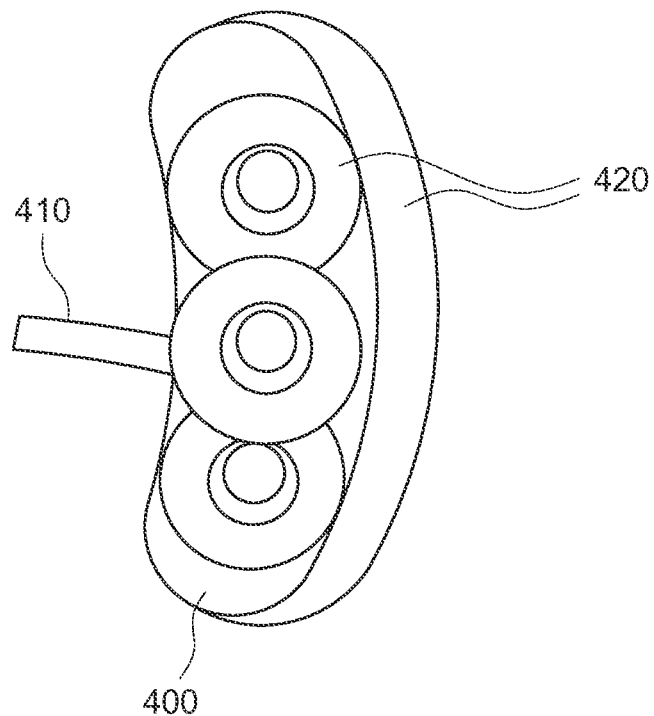
FIG. 23 illustrates a front view of an injection patch, in accordance with one embodiment.

FIGS. 22 and 23 illustrate front views of injection patches, in accordance with one embodiment. The injection patches may be adapted for particular placement on the body and may include injection locations configured to identify an injection site and/or guide placement of the injection device. In some embodiments, the injection patch may be sized and/or shaped for a particular body part. In the embodiment of FIG. 22, the injection patch 300 is a forehead patch. In the embodiment of FIG. 23, the injection patch 400 is an eye patch configured for one or more injections near a user's eye. In alternative embodiments, the injection patch may be a neck patch, a scalp patch, or a combination thereof. In some embodiments, an adhesive may be arranged on a contact surface of the injection patch for adhering the patch to a user's skin and a numbing agent may be provided on the contact surface. The injection patches 300/400 may include registration features 310/410 and holes 320/420.

In general the injection templates or patches may have holes or markings corresponding with injection sites on a body. In some embodiments, the injection templates or patches may be shaped to correspond with a specific location on the body and the holes or markings thus may align with injection sites at that specific location. The holes or markings may be provided so that they appears in the same location on the injection template as positioned on the body as before positioning. The holes or markings may be configured for receiving a needle of the injection device.

In some embodiments, the cartridges in the kit may have varying quantities of botulinum toxin. In some embodiments, the injection locations and cartridges may be color-coordinated or otherwise identified, such that a user may select an appropriate cartridge with an appropriate amount of botulinum toxin for an appropriate injection location.

The holes 320/420 in the injection patch may be sized and configured to receive the leading end of the cartridges or to permit the needle to extend therethrough to penetrate the skin. In some embodiments, the shroud around the needle on the cartridge may have a shape and/or size matching that of the holes in the injection patch. As such, the placement of the injection device with a loaded cartridge may allow for the use of dexterity by the user to ascertain proper positioning of the injection device.

In some embodiments, the holes 320/420 may instead comprise markings where the needle simply pierces the markings. This may be done, for example, where the injection patch or template comprises a relatively flimsy material.

The injection patch may be composed of any suitable material(s) such as paper, plastic, fabric, and/or other suitable materials. The injection patch may generally have a contact surface or side configured to be arranged in contact with a user's skin. An adhesive component may be arranged on at least a portion of the contact surface. The adhesive component may include a relatively mild glue, for example. In some embodiments, the adhesive component may include a silicone-based adhesive, for example. The adhesive component may be arranged over all or a select portion of the contact surface of the patch.

In some embodiments, the injection patch may have a numbing agent arranged on at least a portion of the contact surface, so as to provide a numbing effect to help reduce pain at the injection site. The numbing agent may include lidocaine or a similar anesthetic component in some embodiments. The numbing agent may include, for example, between approximately 1% and 20% lidocaine in an aqueous base. Particularly, for example, the numbing agent may include approximately 5% lidocaine in an aqueous base in some embodiments. In some embodiments, the numbing agent may be combined with the adhesive element on the patch. In other embodiments, the numbing agent may be arranged over a portion of the contact surface of the patch, while the adhesive may be arranged over a different portion of the contact surface of the patch. In still other embodiments, the adhesive component may be arranged over the numbing agent, for example. In some embodiments, the numbing agent may begin to numb a user's skin upon contact.

In some embodiments, the injection patch may include a sponge-like material or other relatively flexible and/or porous material. The sponge-like material may be configured to absorb or retain a quantity of numbing agent. In some embodiments, the contact surface of the patch may include such material. For example, where the numbing agent is an aqueous lidocaine solution, the numbing agent may be arranged within the sponge-like material, and an adhesive may be arranged over the sponge-like material.

It may be appreciated that in some embodiments, an injection patch may have a buffer or a section of the patch that does not contain adhesive or numbing agent. For example, where a patch is configured to be arranged near a user's eye, the patch may have a buffer zone or component, such as a 2 millimeter zone or other appropriately sized zone, arranged nearest the user's eye, so as to mitigate seepage of the numbing agent and/or adhesive near the user's eye. In some embodiments, the buffer may include a portion of the sponge-like material described above.

In some embodiments, a covering, such as a paper or plastic based covering, may be arranged over the adhesive and/or numbing agent on the contact surface of the patch. The covering may be configured to protect the adhesive and/or numbing agent until use by a user. For example, the covering may be a peelable paper based liner.

In some embodiments, one or more injection patches may be shaped, sized, and/or otherwise configured for use at a particular location on the user's body. For example, FIGS. 22 and 23 illustrate examples of a forehead patch 300 and an eye patch 400. Additionally, in some embodiments, the injection patch may have one or more openings 320/420, such that the user may position the syringe needle and inject the botulinum toxin solution through the patch. In this way, the one or more openings on the injection patch may operate as a guide to help users place the injections at the desired locations. As mentioned, the openings may be sized and shaped to receive the leading end of a cartridge, for example.

In some embodiments, the injection patch may be partially or entirely transparent. For example, the injection patch may be transparent with the exception of colored rings around each injection opening.

Figure 24:
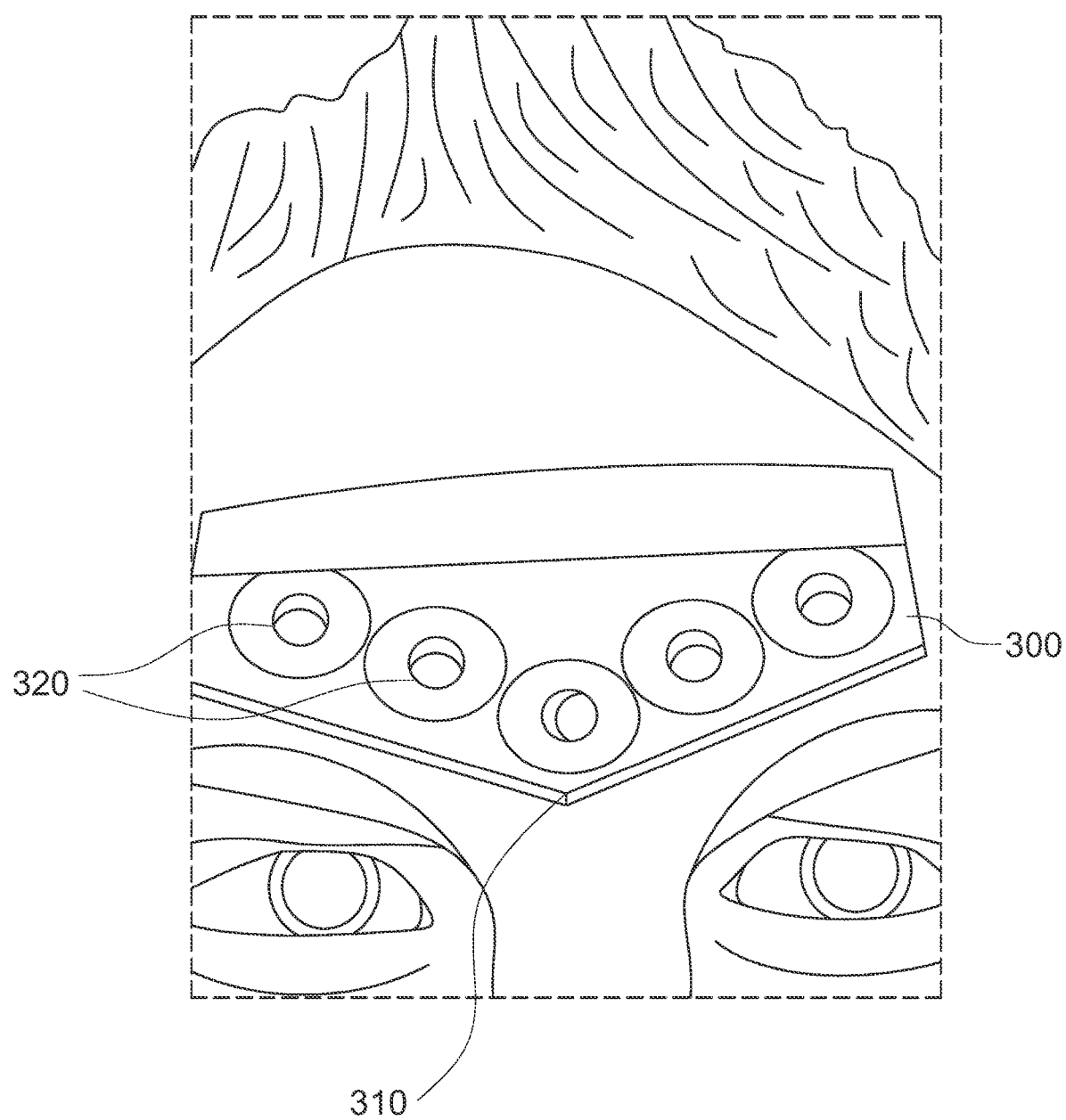
FIG. 24 illustrates a front view of an injection patch arranged on a user's forehead, according to one or more embodiments.

The forehead patch 300 may be configured to be arranged on a user's forehead area, generally above the nose and between the eyes, so as to target skin lines or wrinkles in this area. In some embodiments, the forehead patch may have one or more features to help a user position the patch in the desired location on the user's skin. For example, as shown in FIG. 22, the forehead patch 300 may have a registration feature 310, which may be, for example, a peak configured such that a user may position the peak centrally between the user's eyes and directed at the bridge of the nose. Additionally or alternatively, the forehead patch 300 may have one or more other registration features configured to help a user register the patch with respect to the user's forehead, hairline, eyes, nose, eyebrows, or other facial features. FIG. 24 illustrates a front view of an injection patch 300 arranged on a user's forehead, according to one or more embodiments.

The forehead patch 300 may have one or more openings 320, as shown in FIG. 22. Each opening 320 may be arranged on the patch 300 so as to identify a desired location for an injection. For example, as shown in FIG. 22, in some embodiments, the forehead patch 300 may include 5 injection openings 320 configured to provide a guide for placing injections at 5 locations along the user's forehead. In other embodiments, the forehead patch 300 may include 1, 2, 3, 4, or any other suitable number of injection openings 120. Each opening 320 may generally be large enough for a user to arrange the syringe through the opening, and additionally may be small enough so as to identify a targeted location for the injection. In some embodiments, the openings 320 may be sized to receive the injection device. For example, the openings 320 may be configured such that a user may insert an injection end of the injection device through the opening in the patch. This may help ensure that the injection is placed centrally within the opening 320. The forehead patch 300 may generally be sized and shaped to accommodate the desired number of injection openings and to be arranged comfortably on the user's skin in the desired location. In one or more embodiments, the number of openings in the patch may correspond to the number of cells in the staging template holding the cartridges.

Figure 25:
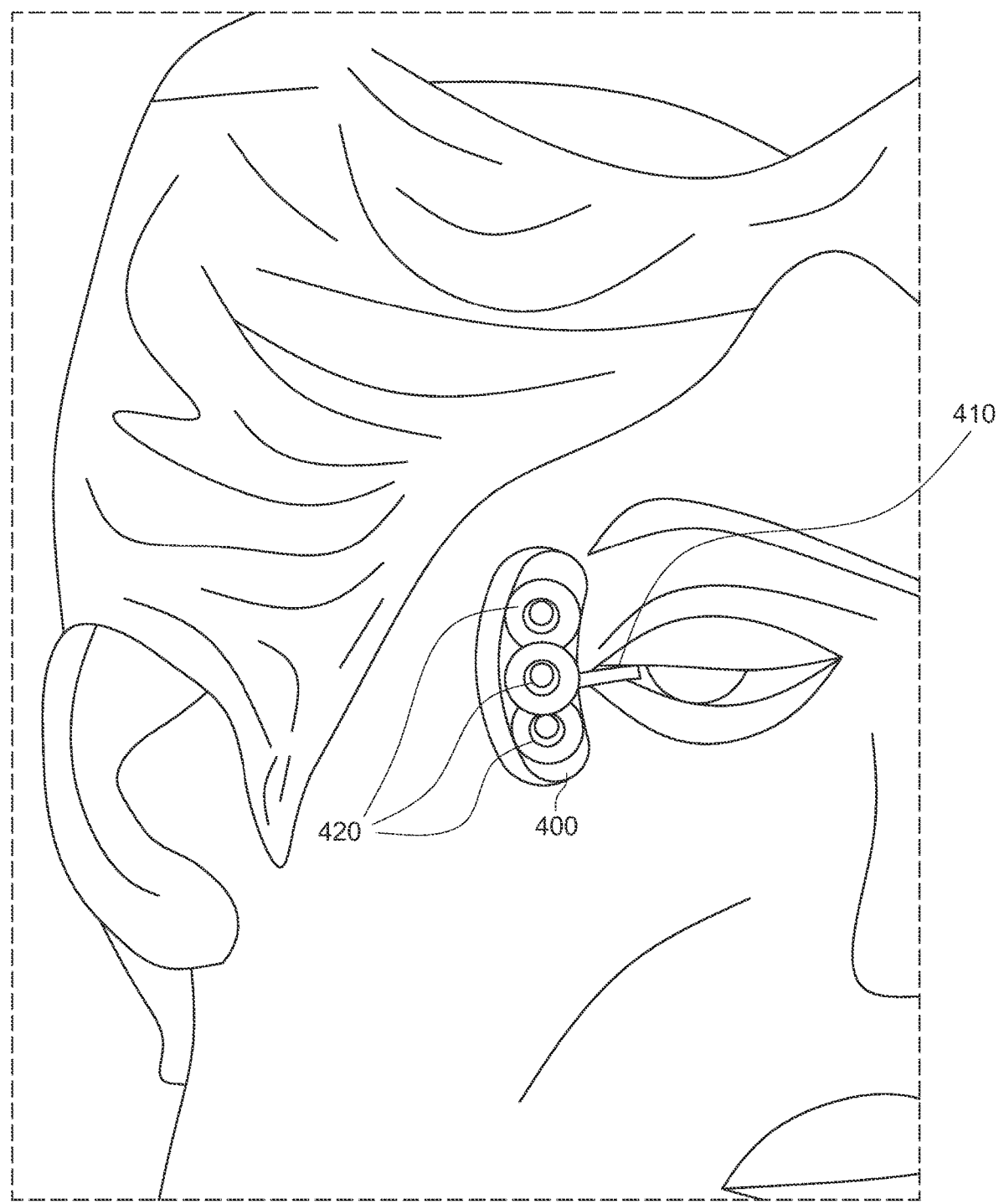
FIG. 25 illustrates a front view of an injection patch arranged on a user's eye area, according to one or more embodiments.

FIG. 25 illustrates a front view of an injection patch 400 arranged on a user's eye area, according to one or more embodiments. The eye patch 400 may be configured to be arranged near a user's eye area, such as alongside a user's eye, so as to target skin lines or wrinkles in this area. In some embodiments, the eye patch 400 may have one or more features to help a user position the patch in the desired location on the user's skin. For example, as shown in FIG. 23, the eye patch 400 may have a registration feature 410, such as for example a tab configured such that a user may position the tab proximate to the corner of the user's eye. As shown for example in FIG. 25, the registration feature 410 may be configured to be positioned at or near an outer corner of the user's eye, so as to position the eye patch 400 in a desired location. In some embodiments, the registration feature 410 may be removable, such that a user may use the tab to accurately position the patch 400, and then remove the tab for comfort and/or ease of injection. In other embodiments, the eye patch 400 may include additional or alternative registration features to help a user register the eye patch with respect to the user's eye, eyebrow, or other facial features.

The eye patch 400 may have one or more openings 420, as shown in FIGS. 23 and 25. Each opening 420 may be arranged on the patch 400 so as to identify a desired location for an injection. For example, in some embodiments, the eye patch 400 may include 3 injection openings 420 configured to provide a guide for placing injections at 3 locations near the user's eye. In other embodiments, the eye patch 400 may include 1, 2, 4, or any other suitable number of injection openings 420. Each opening 420 may generally be large enough for a user to arrange the syringe through the opening, and additionally may be small enough so as to identify a targeted location for the injection. In some embodiments, the openings 420 may be sized to receive the injection device. For example, the openings 420 may be configured such that a user may insert an injection end of the injection device through the opening in the patch 400. This may help ensure that the injection is placed centrally within the opening 420. The eye patch 400 may generally be sized and shaped to accommodate the desired number of injection openings 420 and to be arranged comfortably on the user's skin in the desired location. As with the forehead patch, in one or more embodiments, the number of openings in the patch 400 may correspond to the number of cells in the staging tray or template holding the cartridges.

Figure 26:
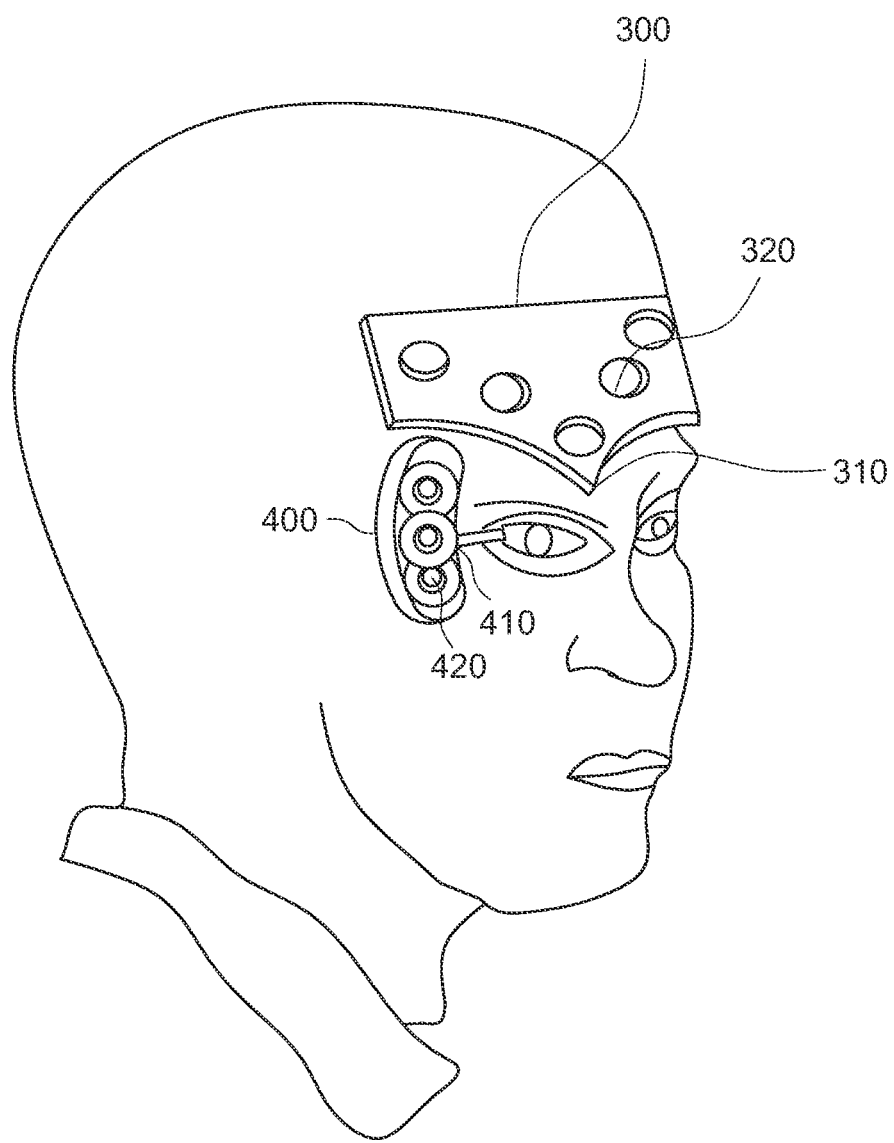
FIG. 26 illustrates a perspective view of an injection patch 300 arranged on a user's forehead and an injection patch 400 arranged on a user's eye area, according to one or more embodiments.

FIG. 26 illustrates a perspective view of an injection patch 300 arranged on a user's forehead and an injection patch 400 arranged on a user's eye area, according to one or more embodiments.

The one or more injection openings 320, 420 on each patch 300, 400 may be color coded or otherwise marked with an identifier. The color coding or other marking(s) of the injection openings may correspond with color coding or other identification of syringes or cartridges, as described above. That is, for example, where one or more cartridges or syringes are prefilled with quantities of botulinum toxin or botulinum toxin solution, the cartridges or syringes may have a color or other identifier to indicate the quantity of solution within the syringe. Such quantities may correspond with particular injection locations. For example, cartridges or syringes having 3 units of botulinum toxin or botulinum toxin solution may have a green cap, ring, sticker, or other component. Correspondingly, injection openings on the eye patch may be identified with a green circle or other component, or the eye patch itself may be green or have a green marker. Similarly, cartridges or syringes having 5 units of botulinum toxin or botulinum toxin solution may have a yellow cap, ring, sticker, or other component, and injection openings on the forehead patch may be identified with a yellow circle or other component. In some embodiments, an injection patch may have injection openings having different colors or other markings. For example, one patch may wrap around a the top and side of a user's eye and may have openings configured for forehead injections and eye injections. This use of corresponding colors or other matching identifiers between injection openings and cartridges or syringes may help a user to inject an appropriate amount of botulinum toxin or botulinum toxin solution at an appropriate location on the user's body. In other embodiments, other quantities and/or identifiers may be used.

While a particular type of system and kit have been described herein, still other approaches to self-administered botulinum toxin or other drugs, medicines, or solutions may be provided. The below discussion includes various other aspects of the system that may be in addition to or an alternative to the above described system.

In some embodiments, the kit may include a predetermined quantity of botulinum toxin. The toxin may be combined in a solution with one or more additional components, such as saline, in some embodiments. The botulinum toxin, saline, and/or other components may be combined in any suitable quantities and ratios. Where cartridges are not provided, for example, the botulinum toxin may be arranged in a bottle or vial, such as an injection vial having a rubberized opening configured to receive a syringe needle, or other container in some embodiments. In other embodiments, the botulinum toxin solution may be arranged within one or more syringes, as described below. In still other embodiments, the kit may exclude the botulinum toxin, such that a user may be required to obtain the solution from a medical professional or other source.

The syringes mentioned may be a standard plunger and barrel syringe having a hollow needle. In some embodiments, the syringe may have a standard barrel and/or needle size. In one or more embodiments, the syringe and/or the above-described cartridges may include a barrel size, or chamber size as the case may be, of 0.3 mL, 0.5 mL, or 1.0 mL. The barrel of the syringe or the chamber of the cartridge may have graduated 1-unit, 0.5-unit, 0.1 mL, or other suitable and/or standard interval. The needle in the syringe or the cartridge may have a gauge ranging between 28 and 31 gauge, and a length ranging between 4 mm and 12.7 mm (0.5 in) in some embodiments. In other embodiments, the syringe or cartridge may have any suitable and/or standard barrel size, needle gauge, and/or needle length. The syringe or cartridge may be sized and generally configured to inject a desired quantity of a botulinum toxin solution. For example, the syringe may be configured to measure and inject between approximately 1 and 10 units of a botulinum toxin solution. Particularly, the syringe or cartridge may be configured to measure and inject between 2 and 7.5 units of a botulinum toxin solution. More particularly, the syringe or cartridge may be configured to measure and inject between 3 and 5 units of a botulinum toxin solution in some embodiments. In other embodiments, the syringe or cartridge may be configured to measure and inject any other suitable quantity of a botulinum toxin solution or another suitable component.

The syringe or cartridge may be configured for single use and thus may be a disposable syringe or cartridge in some embodiments. In other embodiments, the syringe or cartridge may be reusable. In some embodiments, the kit may include a plurality of syringes or cartridges having one or more sizes. In some embodiments, the one or more syringes or cartridges may be pre-filled. That is, the kit may include one or more syringes or cartridges pre-filled with a desired quantity of botulinum toxin or botulinum toxin solution. Multiple syringes or cartridges may have varying quantities of botulinum toxin or solution in some embodiments. For example, some syringes or cartridges may be pre-filled with 3 units of the toxin or solution, while other units may be pre-filled with 5 units of the toxin or solution.

In some embodiments, one or more cartridges or syringes may be particularly identified for a use. Particularly, cartridges or syringes having differing sizes and/or filled with differing botulinum toxin or botulinum toxin solution quantities may be color-coded or otherwise coded or marked to identify their suitability for different uses. For example, syringes or cartridges having 3 units of botulinum toxin or botulinum toxin solution may be color-coded or otherwise coded or marked to identify their suitability for use around a user's eyes or eyelids, and syringes or cartridges having 5 units of botulinum toxin or botulinum toxin solution may be color-coded or otherwise coded or marked to identify their suitability for use around a user's forehead area. In one embodiment, syringes or cartridges may have a colored needle cap, plunger end cap, wrapper, ring, sticker, or other component for identification.

In some embodiments, the kit may include an injection device configured to assist with injection of the botulinum toxin. In some embodiments, the injection device may be an automatic injection device, such as an AUTOJECT device, configured to receive a standard syringe and automatically push the plunger of the syringe to inject the botulinum toxin into the user's muscle or other tissue. In some embodiments, the injection device may be configured to receive a particular syringe size. In this way, the injection device may have an inner width or diameter configured to minimize movement of the syringe within the device. In some embodiments, the injection device may have a ballpoint pen-like design. The injection device may have one or more ergonomic features in some embodiments. The injection device may be a reloadable device, such that the user may perform multiple injections with the device. In other embodiments, the injection device may be a single-use device having, for example, a pre-loaded syringe component. In some embodiments, the injection device may be a spring activated device. For example, a syringe may be loaded within the injection device against a compressed or partially compressed spring. The spring may operate to push the plunger of the syringe so as to expel the botulinum toxin through the needle of the syringe.

The injection device may generally be configured to help a user to safely and effectively deliver an injection of botulinum toxin or another component without, for example, injecting the needle too deep beneath the user's skin. For example, where a user may be injecting botulinum toxin around the eye area, the injection device may help to ensure that the user does not inject the needle too deep around the eyeball or eye socket. The injection device may help to control the direction and angle of the injection. Moreover, the injection device may, in some embodiments, conceal or partially conceal the syringe and/or needle before and/or during an injection. In this way, the injection device may help calm users who may have needle phobias or other difficulties with needles or syringes.

A botulinum toxin self-administration kit or system may be available to a user for at-home use in some embodiments. In other embodiments, such a kit or system may be available to a physician, nurse, or other medical professional for in-clinic or other in-office use, for example. In some embodiments, the kit may be configured for a particular use. For example, some kits may be configured for use with particular areas of the body, such as the eye area, forehead area, neck, scalp, or a combination thereof. In this way, a kit may have one or more patches and one or more syringes, injection devices, and/or botulinum toxin quantities configured for use on the particular area of the body. Other kits may include patches, syringes, injection devices, and/or botulinum toxin quantities for multiple body areas. In some embodiments, kits may have other selectable or variable components or features. For example, some kits may have relatively higher or lower botulinum toxin quantities, number of injections, or patch sizes.

In some embodiments, the present disclosure relates to a method for self-administering a botulinum toxin injection. The method may include requesting a self-administered botulinum toxin kit, selecting an injection patch, positioning the injection patch on the body, selecting a cartridge, engaging the cartridge with the injection device, and injecting the botulinum toxin.

In some embodiments, requesting a self-administered botulinum toxin kit may include obtaining a prescription or medical professional recommendation for botulinum toxin injections. The kit may be requested by a user or the user's medical professional in some embodiments. The kit may be requested by any suitable means, such as through a website, application, email, mail, telephone call, or any other suitable means. As described above, in some embodiments, botulinum toxin kits may be configured for different types of uses or injections. In this way, a user may request a kit particular to the user's needs.

The method for self-administered botulinum toxin injection may additionally include selecting an injection patch. As described above, some injection patches may be configured for particular injection areas or areas of the body. For example, where a user desires to inject botulinum toxin around the user's eye area(s) to target lines or wrinkles around the eye area, the user may select an injection patch particularly configured for the eye area.

The user may position the injection patch on the body area that will receive one or more injections. In some embodiments, the user may remove a covering, such as a protective covering over a contact side of the patch, before positioning the patch. Moreover, as described above, positioning the patch may include registering the injection patch with a body part or feature. For example, the user may align a registration tab, peak, or other element with the user's eye, nose, brow, or other body part or facial feature. In some embodiments, the user may optionally remove the registration tab or other registration element after positioning the injection patch.

The user may select a cartridge for injecting the botulinum toxin. In some embodiments, this may include selecting a prefilled cartridge from a staging tray, based on a desired quantity of botulinum toxin or botulinum toxin solution or a location to be injected. For example, as described above, the user may select a syringe having a color or other identifier matching that of a corresponding injection hole and/or patch color or identifier. In other embodiments, the user may select a cartridge based on size or other factors such as its location in the staging tray that corresponds to a location of an injection. In some embodiments, where a prefilled cartridge is not used, the user may draw a desired quantity of botulinum toxin or solution into the syringe.

The user engages a cartridge with the main body/handle. The user may use the injection device with the cartridge or syringe to inject the botulinum toxin into the user's muscle or other tissue at the desired injection site. This may include positioning the syringe and/or injection device through an injection opening in the patch, pressing the injection device against the skin to release a safety mechanism, and pressing the actuation button of the injection device to cause the injection device to advance the needle into the skin followed by injection of the botulinum toxin or other solution.

It is to be appreciated that, while a variety of embodiments have been described herein, the various features from the different embodiments may be combined. For example, features from a first injection device, as described herein, may be combinable with features of a second injection device described herein.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein, the phrase "at least one of [X] and [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. An injection device for injection of a fluid, the injection device comprising:
   a body portion having a cartridge end and a handle end, the body portion comprising:
      a main body;
      an injection assembly extending through the main body to the cartridge end and effecting insertion of a needle and ejection of the fluid; and
      an actuation button, wherein actuation of the actuation button leads to insertion of the needle and dispensing of the fluid; and
   a cartridge removably couplable to the body portion at the cartridge end, the cartridge comprising;
      a syringe assembly including a drug chamber and a piston, wherein the drug chamber houses the fluid;
      the needle; and
      a needle shield positioned over the needle; and
   a safety mechanism comprising a body portion safety interlock and a cartridge safety interlock, wherein the cartridge safety interlock engages the body portion safety interlock such that the body portion safety interlock releases the actuation button for actuation, wherein the safety mechanism is released upon depression of the needle shield such that the needle may be inserted and the fluid dispensed.

2. The injection device of claim 1, wherein the injection device has multi stage deployment comprising insertion of the needle and injection of the fluid.

3. The injection device of claim 2, wherein the multi stage deployment is activated by actuating the actuation button.

4. The injection device of claim 1, wherein the injection assembly works with the piston of the cartridge to dispense the fluid.

5. The injection device of claim 1, wherein the body portion further comprises a cocking assembly comprising a cocking handle, an end cap, a cocking ring, and a snap ring, and wherein the cocking assembly is provided at the handle end of the body portion.

6. The injection device of claim 1, wherein when the cartridge safety interlock is in a used configuration, the needle shield is locked in a forward position and the cartridge cannot be reused.

7. The injection device of claim 1, wherein the injection assembly further comprises a needle insertion spring and a drug delivery spring.

8. The injection device of claim 1, wherein the cartridge includes an extension piece and the body portion includes an opening piece, wherein the extension piece is received by the opening piece to removably couple the cartridge to the body portion.

9. The injection device of claim 1, wherein the cartridge is predosed with a specific quantity of fluid.

10. The injection device of claim 1, wherein the injection device has multi stage deployment comprising insertion of the needle and injection of the fluid, and wherein the multi stage deployment is triggered by actuation of the actuation button.

11. An injection device for injection of a fluid, the injection device comprising:
a body portion having a cartridge end and a handle end, the body portion comprising:
an injection assembly wherein the injection assembly effects insertion of a needle and ejection of the fluid; and
an actuation button wherein actuation of the actuation button leads to insertion of the needle and dispensing of the fluid;
a cartridge removably couplable to the body portion at the cartridge end, the cartridge comprising;
a syringe assembly including a drug chamber and a piston, wherein the drug chamber houses the fluid;
the needle; and
a needle shield over the needle, the needle shield having an initial position over the needle and a depressed position; and
a safety mechanism configured to prevent dispensing of a fluid, the safety mechanism comprising a body portion safety interlock and a cartridge safety interlock, wherein the cartridge safety interlock engages the body portion safety interlock such that the body portion safety interlock releases the actuation button for actuation, wherein the safety mechanism is released upon proper positioning of the injection device, wherein such release enables the needle to be inserted and the fluid to be dispensed.

12. The injection device of claim 11, wherein proper positioning is achieved when the needle shield is in the depressed position.

13. The injection device of claim 11, wherein the drug chamber is formed of glass and other portions of the cartridge are formed of plastic.

14. The injection device of claim 12, wherein the safety mechanism is reengaged when the needle shield returns to the initial position.

15. The injection device of claim 11, wherein the body portion safety interlock is an electrical switch.

16. An injection device for injection of a fluid, the injection device comprising:
a body portion having a cartridge end and a handle end, the body portion comprising:
a main body;
an injection assembly extending through the main body to the cartridge end and effecting insertion of a needle and ejection of the fluid; and
an actuation button, wherein actuation of the actuation button leads to insertion of the needle and dispensing of the fluid; and
a cartridge removably couplable to the body portion at the cartridge end, the cartridge comprising;
a syringe assembly including a drug chamber and a piston, wherein the drug chamber houses the fluid;
the needle; and
a needle shield positioned over the needle; and
a safety mechanism comprising a body portion safety interlock and a cartridge safety interlock, wherein the cartridge safety interlock comprises a slip ring having pins;
wherein depression of the needle shield causes the needle shield to press back the pins of the cartridge safety interlock wherein said pins engage and release the body portion safety interlock, which in turn allows the actuation button to be pressed to inject the fluid.

* * * * *